(12) United States Patent
Hassan et al.

(10) Patent No.: US 9,205,388 B2
(45) Date of Patent: Dec. 8, 2015

(54) HIGH SHEAR SYSTEM AND METHOD FOR THE PRODUCTION OF ACIDS

(75) Inventors: Abbas Hassan, Sugar Land, TX (US); Aziz Hassan, Sugar Land, TX (US); Rayford G. Anthony, College Station, TX (US); Gregory G. Borsinger, Chatham, NJ (US)

(73) Assignee: H R D Corporation, Houston, TX (US)

( * ) Notice: Subject to any disclaimer, the term of this patent is extended or adjusted under 35 U.S.C. 154(b) by 601 days.

(21) Appl. No.: 12/855,402

(22) Filed: Aug. 12, 2010

(65) Prior Publication Data

US 2010/0324308 A1    Dec. 23, 2010

Related U.S. Application Data

(63) Continuation-in-part of application No. 12/138,154, filed on Jun. 12, 2008, now Pat. No. 8,080,685.

(60) Provisional application No. 61/242,134, filed on Sep. 14, 2009, provisional application No. 60/946,445, filed on Jun. 27, 2007, provisional application No. 60/946,504, filed on Jun. 27, 2007.

(51) Int. Cl.
| | |
|---|---|
| *C07D 307/89* | (2006.01) |
| *B01F 7/00* | (2006.01) |
| *B01F 13/10* | (2006.01) |
| *C07C 51/265* | (2006.01) |

(52) U.S. Cl.
CPC ......... *B01F 7/00766* (2013.01); *B01F 13/1013* (2013.01); *B01F 13/1016* (2013.01); *C07C 51/265* (2013.01); *C07D 307/89* (2013.01)

(58) Field of Classification Search
None
See application file for complete search history.

(56) References Cited

U.S. PATENT DOCUMENTS

| | | | |
|---|---|---|---|
| 3,170,768 A | 2/1965 | Baldwin | |
| 3,627,280 A | 12/1971 | Fridman et al. | |
| 3,887,167 A | 6/1975 | Irwin | |
| 3,931,305 A | 1/1976 | Fisher | |
| 4,158,738 A | 6/1979 | Scott et al. | |
| 4,568,427 A * | 2/1986 | Danz et al. ...................... 203/57 |
| 4,578,511 A | 3/1986 | Rossi et al. | |
| 4,835,307 A | 5/1989 | Lindahl et al. | |
| 4,851,571 A | 7/1989 | Sauer et al. | |
| 4,877,900 A | 10/1989 | Tamaru et al. | |
| 4,900,480 A | 2/1990 | Lawrence et al. | |
| 5,009,816 A | 4/1991 | Weise et al. | |
| 5,371,283 A | 12/1994 | Kingsley et al. | |
| 5,451,348 A | 9/1995 | Kingsley et al. | |
| 5,538,191 A | 7/1996 | Holl | |
| 5,877,350 A | 3/1999 | Langer et al. | |
| 6,241,472 B1 | 6/2001 | Bosch et al. | |
| 6,307,099 B1 | 10/2001 | Turner et al. | |
| 6,368,366 B1 | 4/2002 | Langer et al. | |
| 6,368,367 B1 | 4/2002 | Langer et al. | |
| 6,383,237 B1 | 5/2002 | Langer et al. | |
| 6,530,964 B2 | 3/2003 | Langer et al. | |
| 6,742,774 B2 | 6/2004 | Holl | |
| 6,866,411 B1 | 3/2005 | Stelzer et al. | |
| 7,273,950 B2 | 9/2007 | Varela-Fuentes et al. | |
| 2002/0010364 A1 * | 1/2002 | Braithwaite et al. | |
| 2002/0193630 A1 * | 12/2002 | Lin et al. ...................... 562/414 |
| 2003/0043690 A1 | 3/2003 | Holl | |
| 2004/0052158 A1 | 3/2004 | Holl | |
| 2005/0033069 A1 | 2/2005 | Holl et al. | |
| 2006/0047159 A1 | 3/2006 | Wonders et al. | |
| 2008/0144431 A1 | 6/2008 | Troxler | |
| 2009/0005585 A1 | 1/2009 | Hassan et al. | |
| 2009/0005588 A1 | 1/2009 | Hassan et al. | |
| 2009/0005591 A1 | 1/2009 | Hassan et al. | |
| 2009/0036694 A1 | 2/2009 | Hassan et al. | |
| 2010/0168477 A1 * | 7/2010 | Hassan et al. .................. 568/376 |
| 2010/0234550 A1 * | 9/2010 | Hassan et al. .................. 526/351 |

FOREIGN PATENT DOCUMENTS

| | | |
|---|---|---|
| EP | 0682000 | 11/1995 |
| EP | 0781754 | 7/1997 |
| GB | 1219453 | 1/1971 |
| JP | 62045335 | 2/1987 |

(Continued)

OTHER PUBLICATIONS

IKA—The Company, IKA Proudly Manufactures in the USA Catalog, 2003, pp. 1-38.
Gogate et al. "Cavitation: A Technology on the horizon," Current Science 91 (No. 1): 35-46 (2006).
International Search Report for PCT/US2010/045944 dated Mar. 17, 2011.
Office Action dated Jun. 25, 2009 for U.S. Appl. No. 12/142,447.
Office Action dated Jan. 7, 2010 for U.S. Appl. No. 12/142,447.
Office Action dated May 13, 2010 for U.S. Appl. No. 12/142,447.
Office Action dated Feb. 4, 2010 for U.S. Appl. No. 12/492,721.
Office Action dated Feb. 18, 2010 for U.S. Appl. No. 12/635,433.
Office Action dated Feb. 18, 2010 for U.S. Appl. No. 12/635,454.
Office Action dated May 14, 2010 for U.S. Appl. No. 12/137,441.
Office Action dated Feb. 19, 2010 for U.S. Appl. No. 12/144,459.
Office Action dated Sep. 2, 2009 for U.S. Appl. No. 12/142,433.
Office Action dated Jan. 29, 2010 for U.S. Appl. No. 12/142,433.
Office Action dated May 24, 2010 for U.S. Appl. No. 12/142,433.
Office Action dated Apr. 30, 2010 for U.S. Appl. No. 12/141,191.

(Continued)

*Primary Examiner* — Alicia L Otton
(74) *Attorney, Agent, or Firm* — Timothy S. Westby; Porter Hedges LLP

(57) ABSTRACT

Herein disclosed is a method, comprising: forming a dispersion under high shear comprising gas bubbles of an oxidant dispersed in a liquid phase, wherein the bubbles have a mean diameter of less than 1.5 micron; and contacting the dispersion with an oxidation catalyst to produce a product stream, wherein the product stream comprises a substance selected from the group consisting of dicarboxylic acid, benzoic acid, 2-methylbenzoic acid, 3-methylbenzoic acid, 4-methylbenzoic acid, and phthalic anhydride. In some cases, forming the dispersion under high shear comprises introducing the oxidant and the liquid phase into a high shear device comprising at least one rotor and at least one complementarily-shaped stator. Herein also disclosed is a system for producing a substance selected from the group consisting of dicarboxylic acid, benzoic acid, 2-methylbenzoic acid, 3-methylbenzoic acid, 4-methylbenzoic acid, and phthalic anhydride.

7 Claims, 6 Drawing Sheets

(56) References Cited

FOREIGN PATENT DOCUMENTS

| KR | 1020020004001 | | 1/2002 | |
|---|---|---|---|---|
| WO | 9838150 | | 9/1998 | |
| WO | 02064708 | | 8/2002 | |
| WO | WO 2010/077823 | * | 7/2010 | ............... B01J 19/18 |

OTHER PUBLICATIONS

Office Action dated Oct. 27, 2009 for U.S. Appl. No. 12/142,120.
Office Action dated May 5, 2010 for U.S. Appl. No. 12/571,537.
Office Action dated Feb. 24, 2011 for U.S. Appl. No. 12/796,358.
Office Action dated Feb. 29, 2012 for U.S. Appl. No. 12/146,733.
Office Action dated Jun. 3, 2011 for U.S. Appl. No. 12/568,155.
Office Action dated Jun. 2, 2011 for U.S. Appl. No. 12/427,286.
Office Action dated Jun. 3, 2011 for U.S. Appl. No. 12/568,280.
International Search Report and Written Opinion dated Aug. 28, 2008 for corresponding International Application No. PCT/US2008/066905 (7 pgs.).
GCC Examination Report dated Oct. 8, 2011 for corresponding GCC Application No. GCC/P/2008/1168 (4 pgs.).
European Search Report dated Apr. 23, 2012 for corresponding European Application No. 08771007.5 (7 pgs.).
Chattopadhyay et al., "Understanding Mechanical Energy Driven Nonequilibrium Processing: Some Results, Eleventh International Conference on Rapidly Quenched and Metastable Materials," A Material Science and Engineering, vol. 375-377, dated Jul. 15, 2004, pp. 72-77 (9 pgs.).
European Search Report dated Jan. 22, 2014 for corresponding European Application No. 10815810.6-1451 / 2477958 (6 pgs.).
International Preliminary Report on Patentability dated Mar. 29, 2012 for corresponding International Application No. PCT/US2010/045944 (5 pgs.).

* cited by examiner

HIGH SHEAR SYSTEM AND METHOD FOR THE PRODUCTION OF ACIDS

CROSS-REFERENCE TO RELATED APPLICATIONS

This application claims the benefit under 35 U.S.C. §119(e) of U.S. Provisional Patent Application No. 61/242,134 filed Sep. 14, 2009; and is a continuation-in-part of U.S. patent application Ser. No. 12/138,154, filed Jun. 12, 2008, which claims the benefit under 35 U.S.C. §119(e) of U.S. Provisional Patent Application No. 60/946,445 filed Jun. 27, 2007, and U.S. Provisional Patent Application No. 60/946,504 filed Jun. 27, 2007, the disclosures of which are hereby incorporated herein by reference.

STATEMENT REGARDING FEDERALLY SPONSORED RESEARCH OR DEVELOPMENT

Not Applicable.

BACKGROUND

1. Technical Field

The present invention relates to systems and methods for the production of acids, such as aromatic carboxylic acids. More particularly, the present invention relates to the high shear production of aromatic carboxylic acids (e.g., terephthalic acid) which are sparingly soluble in acetic acid; the production of benzoic acid via gas/liquid phase partial oxidation of toluene; the production of methylbenzoic acid isomers and phthalic acid isomers from the corresponding xylene isomers; and more particularly to the acceleration of such reactions by high shear mixing.

2. Background of the Invention

Terephthalic acid is one of three isomeric organic phthalic compounds having the formula $C_6H_4(COOH)_2$. Terephthalic acid is the para-form of phthalic acid, also known as 1,4-benzenecarboxylic acid, benzene-1,4-dicarboxylic acid, para-phthalic acid, TPA, and PTA. Terephthalic acid is a commodity chemical, used primarily as a precursor to the polyester polymers, primarily polyethylene terephthalate (PET), that are used to make clothing and bottles. Terephthalic acid has also been utilized for various purposes in addition to the fiber field and PET-bottle production, specifically for the production of PET-film and engineering plastics, as well as for a poultry feed additive. Phthalic acid derivatives are also routinely utilized in the production of dyes, medicine, synthetic perfumes, pesticides, and other chemical compounds.

Current state-of-the art technology for the manufacture of terephthalic acid involves the liquid phase oxidation of p-xylene feedstock using molecular oxygen or air in a solvent comprising lower C2 to C6 aliphatic mono-carboxylic acid, usually acetic acid, in the presence of a dissolved heavy metal (e.g. cobalt and/or manganese) catalyst system incorporating a promoter such as bromine. The reaction is carried out in at least one stirred vessel under elevated temperature and pressure conditions, typically 150° C. to 250° C. and 6 to 30 bars respectively, with air being sparged into the reaction mixture. The process typically produces terephthalic acid in high yield, e.g. at least 95%. Isothermal reaction conditions are generally maintained in the oxidation vessel by allowing evaporation of the solvent, together with water produced in the reaction. The resulting vapor is condensed and returned to the reaction vessel as reflux. Terephthalic acid is only sparingly soluble in the solvent and a substantial proportion of the product typically precipitates during the course of the reaction in conventional production methods. As a result of such precipitation, impurities such as 4-carboxybenzaldehyde (also known as 4-CBA, benzaldehyde-4-carboxylic acid, and terephthalaldehydic acid) and color bodies, including p-toluic acid, co-precipitate with the terephthalic acid, producing a crude product which generally must be purified to meet end-use requirements, e.g. requirements of polyester producers.

Purification typically comprises dissolving the oxidation product comprising crude terephthalic acid in water and, under elevated temperature and pressure, contacting the aqueous solution with hydrogen in the presence of a hydrogenation catalyst. The purified terephthalic acid is typically recovered thereafter by crystallization (cooling in a stepwise manner) and various solid-liquid separation techniques.

Accordingly, there is a need in the industry for enhanced systems and processes of producing aromatic carboxylic acids, such as terephthalic acid. Desirably, the system and method allow for minimal or substantially no purification being required downstream of the oxidation to meet purity requirements. Systems and methods for production of purified terephthalic acid without the need for extensive downstream purification and/or with reduced size (and thus cost) oxidation apparatus are desirable so as to more economically provide purified terephthalic acid.

Benzoic acid (carboxybenzene) is used to make a large number of chemicals. For example, benzoic acid is used to produce benzoyl chloride, by treatment of benzoic acid with thionyl chloride, phosgene or one of the chlorides of phosphorus. Benzoyl chloride is an important starting material for several benzoic acid derivates like benzyl benzoate, which is used for artificial flavors and insect repellents. Benzoyl peroxide is obtained by treatment of benzoic acid with peroxide. The peroxide is useful as a radical starter in polymerization reactions and also a component in cosmetic products. Benzoate plasticizers, such as the glycol-, diethylenegiveol- and triethyleneglycol esters are obtained by transesterification of methyl benzoate with the corresponding diol. Alternatively these species arise by treatment of benzoylchloride with the diol. These plasticizers are used similarly to those derived from terephthalic acid ester. Phenol is obtained by oxidative decarboxylation of benzoic acid at 300° C. to 400° C. Benzoic acid is also used as a food preservative, and as a constituent of ointments for the treatment of fungal skin diseases and acne.

The methylbenzoic acids are used in various industrial processes, including the production of chemicals, drugs, paints, and enamels. 4-Methylbenzoic acid (p-toluic acid) is a substituted benzoic acid that is used in the chemical industry to make terephthalic acid, which, in turn, is used industrially to produce polyethylene terephthalate (PET). PET is a thermoplastic polymer resin of the polyester family and is an important raw material used in synthetic fibers. It is also used in the manufacture of a wide variety of containers, in thermoforming applications, and in resins combined with glass fiber. 3-methylbenzoic acid (m-toluic acid) is used industrially as a precursor in the production of the insecticide DEET (N,N diethyl-m-toluamide), among other uses. 2-methylbenzoic acid (o-toluic acid) is widely used as a raw material for agricultural chemicals, medicines and polymerization initiators.

Benzoic acid and the 2-, 3-, and 4-methylbenzoic acid isomers are typically produced by partially oxidizing toluene or o-, m-, and p-xylene, respectively, with oxygen or air. On an industrial scale, both of the methyl groups in p-xylene are oxidized by oxygen or air to produce terephthalic acid (benzene-1,4-dicarboxylic acid or p-phthalic acid). Such processes are strongly influenced by a number of factors, such as temperatures, pressures, and the nature of the catalyst used, if any. Appropriate selection of these factors is important, as selection influences the reaction trend, the reaction velocity, and the overall technical and economic balance of the production, both in terms of yield and catalyst consumption, and also from the point of view of the intricacy and costs of installation and upkeep. These costs are influenced, for example, by the pressures attained, the consumption of thermal energy for reaching desired temperatures, and the intricacy and the number of component parts of the installation. For instance, in many applications it is desirable to enhance the degree of conversion of toluene or xylene. While increasing the reaction pressure may increase reaction rate, it also increases wear of the materials constituting the reactors, the piping, and the mechanical parts of the plant, as well as any ancillary devices. Most existing processes and production facilities for making benzoic, methylbenzoic acids, and phthalic acids are subject to a variety of constraints such as product yield, plant size, energy consumption and mass flow limitations. Accordingly, there is continuing interest in improving the ways that benzoic acid, methylbenzoic acid isomers, and phthalic acid isomers are produced.

SUMMARY

Herein disclosed is a method, comprising: forming a dispersion under high shear comprising gas bubbles of an oxidant dispersed in a liquid phase, wherein the bubbles have a mean diameter of less than 1.5 micron; and contacting the dispersion with an oxidation catalyst to produce a product stream, wherein the product stream comprises a substance selected from the group consisting of dicarboxylic acid, benzoic acid, 2-methylbenzoic acid, 3-methylbenzoic acid, 4-methylbenzoic acid, and phthalic anhydride. In some cases, forming the dispersion under high shear comprises introducing the oxidant and the liquid phase into a high shear device comprising at least one rotor and at least one complementarily-shaped stator.

In embodiments, the oxidant is an oxygen-containing gas. In some cases, the oxidant is selected from the group consisting of oxygen-enriched air, oxygen, and air. In embodiments, the liquid phase comprises water, an aliphatic monocarboxylic acid, aqueous acetic acid, a dicarboxylic acid precursor, toluene, o-xylene, m-xylene, p-xylene, or naphthalene. In some cases, the dicarboxylic acid precursor comprises paraxylene. In some cases, the dicarboxylic acid is terephthalic acid.

In some embodiments, the product stream further comprises impurities selected from p-toluic acid and 4-CBA and the method further comprises purifying terephthalic acid from the product stream. In some cases, further purifying the terephthalic acid comprises one or more steps selected from the group consisting of: forming an aqueous solution comprising water and the terephthalic acid product; hydrogenating the aqueous solution to provide a hydrogenated product; crystallizing the hydrogenated product to provide a crystallization product; and separating crystals of purified terephthalic acid from the crystallization product. In some embodiments, the method further comprises purifying phthalic anhydride from the product stream.

In some embodiments, forming the dispersion and contacting the dispersion with an oxidation catalyst take place substantially simultaneously. In some cases, the method comprises introducing the oxidation catalyst into the high shear device in which the dispersion is formed. In some cases, the high shear device comprises a catalytic surface comprising the oxidation catalyst.

In some embodiments, the 2-, 3- or 4-methylbenzoic acid is an intermediate compound, and the method further comprises subjecting any unreacted o-, m-, or p-xylene and the intermediate compound to further oxidization, to form 1,2-benzenedicarboxylic acid, 1,3-benzenedicarboxylic acid, or 1,4-benzenedicarboxylic acid.

Herein also disclosed is a system for producing a substance selected from the group consisting of dicarboxylic acid, benzoic acid, 2-methylbenzoic acid, 3-methylbenzoic acid, 4-methylbenzoic acid, and phthalic anhydride, the system comprising: at least one high shear device (HSD) comprising at least one rotor and at least one complementarily-shaped stator and configured to subject an oxidant gas and a liquid phase to high shear to produce a dispersion comprising gas bubbles of the oxidant gas with a mean diameter of less than 1.5 micron; wherein the HSD is capable of providing a shear rate of at least $10,000\ s^{-1}$, wherein the shear rate is defined as the tip speed divided by the shear gap, and wherein the tip speed is defined as $\pi Dn$, where D is the diameter of the at least one rotor and n is the frequency of revolution; and a pump configured for delivering the liquid phase to the HSD. In some embodiments, the HSD comprises a catalytic surface comprising an oxidation catalyst.

In some embodiments, the system further comprises a vessel configured to receive the dispersion from the HSD. In some cases, the vessel is a fixed-bed reactor and comprises an oxidation catalyst. In some embodiments, the system further comprises at least one separator configured to receive the dispersion from the HSD. In some embodiments, the system further comprises one or more apparatus downstream of the at least one separator, the one or more apparatus selected from the group consisting of hydrogenation apparatus, crystallization apparatus, evaporators, and solid-liquid separators.

These and other embodiments and potential advantages will be apparent in the following detailed description and drawings.

BRIEF DESCRIPTION OF THE DRAWINGS

For a more detailed description of the preferred embodiment of the present invention, reference will now be made to the accompanying drawings, wherein.

NOTATION AND NOMENCLATURE

Figure 1:
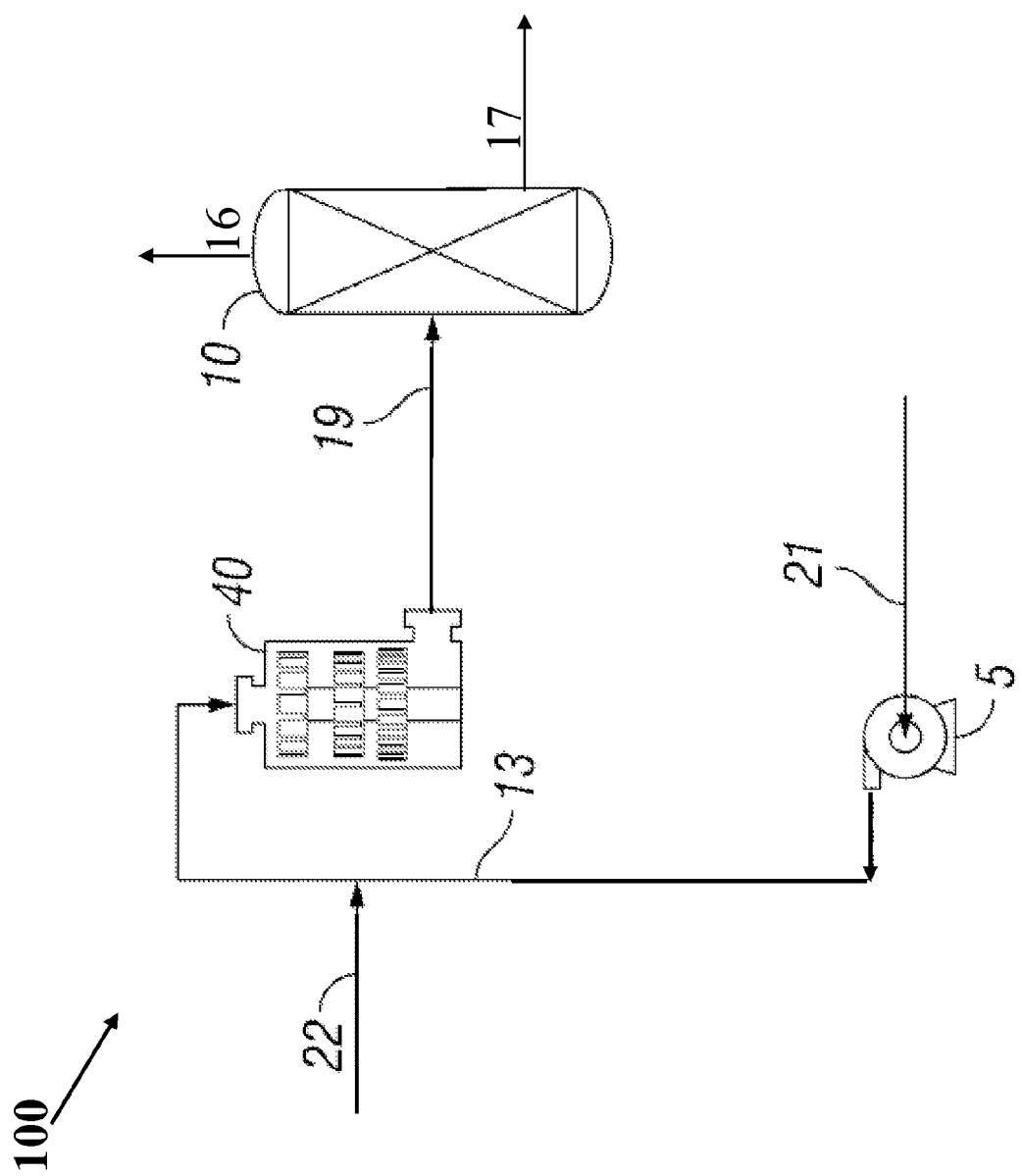
FIG. 1 is a schematic of a high shear system comprising an external high shear mixer/disperser according to an embodiment of the present disclosure.

As used herein, the term 'dispersion' refers to a liquefied mixture that contains at least two distinguishable substances (or 'phases'). As used herein, a 'dispersion' comprises a 'continuous' phase (or 'matrix'), which holds therein discontinuous droplets, bubbles, and/or particles of the other phase or substance. The term dispersion may thus refer to foams comprising gas bubbles suspended in a liquid continuous phase, emulsions in which droplets of a first liquid are dispersed throughout a continuous phase comprising a second liquid with which the first liquid is immiscible, and continuous liquid phases throughout which solid particles are distributed. As used herein, the term "dispersion" encompasses continuous liquid phases throughout which gas bubbles are distributed, continuous liquid phases throughout which solid particles are distributed, continuous phases of a first liquid throughout which droplets of a second liquid that is substantially insoluble in the continuous phase are distributed, and liquid phases throughout which any one or a combination of solid particles, immiscible liquid droplets, and gas bubbles is distributed. Hence, a dispersion can exist as a homogeneous mixture in some cases (e.g., liquid/liquid phase), or as a heterogeneous mixture (e.g., gas/liquid, solid/liquid, or gas/solid/liquid), depending on the nature of the materials selected for combination. A dispersion may comprise, for example, bubbles of gas (e.g. oxidant) in a liquid (e.g. medium comprising terephthalic acid precursor and optionally oxidation catalyst) and/or droplets of one fluid in a phase with which it is immiscible.

The term "catalytic surface" is used herein to refer to a surface in a device that is constructed with catalytic material (such as metals, alloys, etc.) so that catalytic activity is manifested when suitable substance comes in touch with said catalytic surface. The use of the term "catalytic surface" in this document includes all such surfaces regardless of the shape and size of surface, material of construct, method of make, degree of activity, or purpose of use.

Use of the phrase, 'all or a portion of' is used herein to mean 'all or a percentage of the whole' or 'all or some components of'

DETAILED DESCRIPTION

Production of Dicarboxylic Acid

Herein disclosed is a method of producing a dicarboxylic acid, the method comprising: subjecting a feed mixture comprising a precursor of the dicarboxylic acid and a medium to high shear in the presence of an oxidant whereby the dicarboxylic acid precursor is oxidized to produce an high shear product comprising the dicarboxylic acid; introducing the high shear product into a vessel; extracting a product stream comprising dicarboxylic acid and medium from the vessel; and removing the medium from the product stream to provide a dicarboxylic acid product. In embodiments, the dicarboxylic acid is terephthalic acid. In embodiments, the terephthalic acid product further comprises impurities selected from p-toluic acid and 4-CBA and the method further comprises further purifying the terephthalic acid product. In embodiments, further purifying the terephthalic acid product comprises one or more selected from the group consisting of; forming an aqueous solution comprising water and the terephthalic acid product; hydrogenating the aqueous solution to provide a hydrogenated product; crystallizing the hydrogenated product to provide a crystallization product; and separating crystals of purified terephthalic acid from the crystallization product. In embodiments, the terephthalic acid product comprises a total of less than 900 ppmw of p-toluic acid and 4-CBA.

In embodiments, the oxidant is selected from oxygen-containing gases. In embodiments, the oxidant is selected from the group consisting of oxygen-enriched air, oxygen and air. In embodiments, the medium comprises water and an aliphatic monocarboxylic acid. In embodiments, the medium comprises aqueous acetic acid. The ratio of the medium to dicarboxylic acid precursor in the feed mixture may be greater than about 25:1. In embodiments, the dicarboxylic acid precursor comprises paraxylene.

In embodiments, subjecting the feed mixture to high shear in the presence of an oxidant further comprises subjecting the feedstock oil to a shear rate of at least 10,000 s$^{-1}$. Subjecting the feed mixture to high shear in the presence of an oxidant may comprise a shear rate of at least 20,000 s$^{-1}$. In embodiments, subjecting the feed mixture to high shear comprises introducing the feed mixture and the oxidant into a high shear device comprising at least one rotor and at least one complementarily-shaped stator. In embodiments, high shear comprises a shear rate of at least 10,000 s$^{-1}$, wherein the shear rate is defined as the tip speed divided by the shear gap, and wherein the tip speed is defined as $\pi Dn$, where D is the diameter of the at least one rotor and n is the frequency of revolution. In embodiments, high shear comprises a shear rate of at least 20,000 s$^{-1}$. In embodiments, subjecting the feed mixture to a shear rate of at least 10,000 s$^{-1}$ produces a local pressure of at least about 1034.2 MPa (150,000 psi) at a tip of the at least one rotor.

In embodiments, subjecting the feed mixture to high shear comprises providing a tip speed of the at least one rotor of at least about 23 msec, wherein the tip speed is defined as $\pi Dn$, where D is the diameter of the at least one rotor and n is the frequency of revolution. Removing the medium from the product stream may comprise evaporating the medium.

In embodiments, the high shear product comprises a dispersion of oxidant bubbles. In embodiments, the oxidant bubbles have an average diameter that is less than about 1 micron. In embodiments, the oxidant bubbles have an average diameter that is less than about 0.5 micron. In embodiments, the feed mixture further comprises an oxidation catalyst.

Also disclosed herein is an improvement to a process for producing a dicarboxylic acid, said process comprising the steps of oxidizing a dicarboxylic acid precursor by contacting a feed mixture with an oxidant to produce an oxidation product, the feed mixture comprising the dicarboxylic acid precursor, a medium, and optionally an oxidation catalyst; separating the medium from the oxidation product to provide a crude dicarboxylic acid product, providing an aqueous solution of the crude dicarboxylic acid product; hydrogenating the aqueous solution whereby impurities in the crude dicarboxylic acid product are hydrogenated, providing a hydrogenated product; crystallizing the hydrogenated product; and removing crystals of purified dicarboxylic acid from the crystallized product: the improvement comprising subjecting the oxidant and the feed mixture to a shear rate of at least 10,000 s$^{-1}$ during contacting. The dicarboxylic acid is, in embodiments, terephthalic acid and the dicarboxylic acid precursor comprises paraxylene.

Also disclosed herein is a system for production of dicarboxylic acid, the system comprising: at least one high shear device comprising at least one rotor and at least one complementarily-shaped stator and configured to subject a feed mixture comprising a dicarboxylic acid precursor and a liquid medium to high shear in the presence of an oxidant and produce a high shear-treated product comprising dicarboxylic acid, wherein the at least one high shear device is configured to subject the contents therein to a shear rate of at least 10,000 s$^{-1}$, wherein the shear rate is defined as the tip speed divided by the shear gap, and wherein the tip speed is defined as $\pi Dn$, where D is the diameter of the at least one rotor and n is the frequency of revolution; and at least one separator configured to separate vapor or medium from the high shear treated product, providing a medium-reduced oxidation product comprising dicarboxylic acid. In embodiments, the at least one rotor is configured to provide a tip speed of at least about 23 msec. In embodiments, the at least one rotor is configured to provide a tip speed of at least about 40 msec. In embodiments, the at least one rotor is separated from the at least one stator by a shear gap of less than about 5 µm, wherein the shear gap is the minimum distance between the at least one rotor and the at least one stator. In embodiments, the shear rate provided by rotation of the at least one rotor during operation is at least 20,000 s$^{-1}$. The system may further comprise one or more apparatus downstream the at least one separator, the one or more apparatus selected from the group consisting of hydrogenation apparatus, crystallization apparatus, evaporators and solid/liquid separators. In embodiments, the one or more downstream apparatus comprises hydrogenation apparatus. In embodiments, the hydrogenation apparatus comprises at least one high shear device comprising at least one rotor and at least one complementarily-shaped stator and configured to subject the medium-reduced oxidation product to high shear in the presence of hydrogen and produce a hydrogenated product comprising dicarboxylic acid, wherein the at least one high shear device is configured to subject the contents therein to a shear rate of at least 10,000 s$^{-1}$, wherein the shear rate is defined as the tip speed divided by the shear gap, and wherein the tip speed is defined as $\pi Dn$, where D is the diameter of the at least one rotor and n is the frequency of revolution.

In embodiments, the dicarboxylic acid is terephthalic acid. In embodiments, the dicarboxylic acid precursor comprises paraxylene and the liquid medium comprises aqueous acetic acid. The feed mixture may further comprise an oxidation catalyst.

Certain embodiments of the above-described methods or systems potentially provide overall cost reduction by reducing the size and/or number of downstream purification apparatus/steps, providing oxidation product comprising terephthalic acid having reduced levels of impurities, permitting operation at low temperature and/or pressure, and/or reducing capital and/or operating costs of oxidation and/or downstream purification.

Overview. Herein disclosed are a system and a method of producing aromatic carboxylic acids, which are sparingly soluble in acetic acid, by high shear oxidation of a carboxylic acid precursor. Although suitable for the production of a variety of aromatic carboxylic acids, description will be provided with respect to the production of purified terephthalic acid (hereinafter PTA) from a terephthalic acid precursor (hereinafter TAP). The disclosed system and method are applicable to production of PTA from terephthalic acid precursor comprising para-diderivatives of benzene. The disclosed system and method may also be utilized for production of other dicarboxylic acids, for example, isophthalic acid. High shear contacting of TAP with oxidant in the manner as described herein and/or via the disclosed system may allow reduction in the extent and/or number of purification steps required to provide PTA from the crude terephthalic acid product produced by oxidation. In embodiments, utilization of the disclosed system and method may eliminate the need for downstream processing to further purify the terephthalic acid in the oxidation product. The disclosed system and method can thus reduce the cost associated with production of terephthalic acid.

The system comprises an external high shear mechanical device to provide rapid contact and mixing of reactants in a controlled environment in the reactor/mixer device. In embodiments, the system and method allow oxidation at lower temperatures and/or pressures than conventional methods. In embodiments, oxidation is performed at substantially atmospheric global operating conditions. A reactor assembly that comprises an external high shear device (HSD) or mixer as described herein may decrease mass transfer limitations and thereby allow faster oxidation of dicarboxylic acid precursor. In addition to increased mass transfer, energy generated and transferred from the HSD to the reactants may result in a reduction in the temperature to promote the reaction. As mentioned above, enhancing contact via the use of high shear may provide suitable TA directly (i.e., requiring no further purification) or may provide TA requiring reduced downstream purification than oxidation product formed by conventional systems and methods.

High Shear System for Production of Purified Terephthalic Acid. A high shear system 100 for production of terephthalic acid will now be described with reference to FIG. 1, which is a schematic flow diagram of the equipment which can be present in a high shear system 100 according to an embodiment of this disclosure. The basic components of a representative system include external high shear device (HSD) 40 and vessel 10. Terephthalic acid production system 100 (hereinafter TAPS 100) may further comprise pump 5. As indicated in FIG. 2, which is a schematic of a high shear system 100A comprising an external high shear mixer/disperser according to another embodiment of the present disclosure, the system may further comprise downstream purification equipment. In the embodiment of FIG. 2, terephthalic acid production system 100A comprises downstream processing equipment including separation apparatus 50, hydrogenation apparatus 60, crystallization apparatus 70, and solid/liquid separator 80. Each of these components of high shear systems 100/100A are described in more detail hereinbelow.

Line 21 is connected to pump 5 for introducing feed mixture into pump 5. The feed mixture comprises a dicarboxylic acid precursor (e.g. a terephthalic acid precursor) and a suitable medium. The dicarboxylic acid precursor may be selected from para-diderivatives of benzene. In embodiments, the dicarboxylic acid precursor is selected from dialkyl benzene compounds. In embodiments, the TAP comprises p-xylene. Suitable mediums include, but are not limited to, aliphatic monocarboxylic acids (e.g. containing 2 to 6 carbon atoms) and may for instance be selected from acetic acid, propionic acid, butyric acid, isobutyric acid, n-valeric acid, trimethylacetic acid, caprioic acid and mixtures of one or more of these carboxylic acids with water, which is also produced during oxidation. In embodiments, the medium comprises acetic acid and water. In embodiments, the medium comprises aqueous benzoic acid, e.g. a mixture of benzoic acid and water. The feed mixture may further comprise a suitable oxidation catalyst, as discussed further hereinbelow.

Line 13 connects pump 5 to HSD 40, and line 19 carries a high shear-treated stream out of HSD 40. Flow line 19 is any line into which the high shear-treated stream from HSD 40 (comprising dispersion of oxidant in feed mixture) flows. One or more dispersible gas lines 22 are configured to introduce oxidant into HSD 40. The oxidant may be selected from oxygen-containing gases, or may be liquid, such as hydrogen peroxide, in certain applications. Line(s) 22 may introduce oxidant into HSD 40 directly or may introduce oxidant into line 13.

Vessel 10 is fluidly connected to HSD 40 via high shear-treated product flow line 19. Vessel 10 may comprise one or more outlet lines. For example, in the embodiment of FIG. 1, vessel 10 comprises vessel outlet line 16 and oxidation product outlet line 17. As mentioned hereinabove, the high shear system may further comprise downstream purification apparatus. In the embodiment of FIG. 2, system 100A comprises separation apparatus 50 configured to separate terephthalic acid from reaction medium, hydrogenation apparatus 60 configured for catalytic hydrogenation, crystallization apparatus 70 configured to recrystallize terephthalic acid crystals, and solid/liquid separator 80 to separate solid high purity terephthalic acid crystals from liquid. In embodiments, the terephthalic acid in the oxidation product exiting HSD 40 is of a purity that the only downstream processing equipment utilized is a separation vessel configured to separate terephthalic acid from the high shear product exiting HSD 40 and/or vessel 10.

In embodiments, the high shear terephthalic acid production system further comprises separation apparatus 50. Separation apparatus 50 is fluidly connected with HSD 40 outlet line 19, for example via oxidation product outlet line 17. Separation apparatus 50 comprises reaction medium outlet line 54 and separated product outlet line 56 for separated product comprising terephthalic acid (TA). Separation apparatus 50 may further comprise one or more inlet lines 52, for example, for providing an aqueous medium.

In embodiments, the high shear terephthalic acid production system further comprises hydrogenation apparatus 60. Separation apparatus 50 may be fluidly connected with hydrogenation apparatus 60, for example, via separated product outlet line 56. Hydrogenation apparatus 60 comprises gas inlet line 62 and hydrogenation product outlet line 64. The high shear PTA production system may further comprise crystallization apparatus 70. Hydrogenation apparatus 60 may be fluidly connected with crystallization apparatus 70, for example, via hydrogenation product outlet line 64. Crystallization apparatus 70 comprises one or more evaporated solvent outlet lines 72 and a crystallized TA product line 74.

The high shear terephthalic acid production system may further comprise one or more solid/liquid separators 80, configured to separate solid purified terephthalic acid crystals from liquid. Crystallization apparatus 70 may be fluidly connected with solid/liquid separator 80 via crystallized TA product line 74. Solid/liquid separator 80 comprises liquid outlet line 82 and purified terephthalic acid outlet line 84.

Additional components or process steps can be incorporated between HSD 40 and vessel 10 or ahead of pump 5 or HSD 40, if desired, as will become apparent upon reading the description of the high shear process hereinbelow. For example, as indicated in FIG. 2, line 17 can be connected to line 21 or line 13 from high shear product flow line 19 and/or from vessel 10 oxidation product outlet line 17, for example via a line 17A, such that oxidation product comprising TA may be recycled to HSD 40. PTA may be removed from system 100 via, for example, vessel 10 oxidation product outlet line 17, separated product outlet line 56, or PTA outlet line 84.

High Shear Device 40. High shear terephthalic acid production system 100 comprises one or more high shear devices 40. External high shear device (HSD) 40, also sometimes referred to as a high shear mixer, is configured for receiving an inlet stream, via line 13. One or more line(s) 22 may be configured to introduce oxidant into HSD 40. Alternatively, HSD 40 may be configured for receiving feed mixture and oxidant via separate inlet lines. Although only one HSD is shown for contacting oxidant and feed mixture in the embodiment of FIG. 1, it should be understood that some embodiments of the system can comprise two or more HSDs for contacting feed mixture and oxidant. The two or more HSDs 40 can be arranged in either series or parallel flow. In embodiments, high shear terephthalic acid production system 100 comprises a single HSD 40.

HSD 40 is a mechanical device that utilizes one or more generators comprising a rotor/stator combination, each of which has a gap between the stator and rotor. The gap between the rotor and the stator in each generator set may be fixed or may be adjustable. HSD 40 is configured in such a way that it is capable of effectively contacting the components therein at rotational velocity. The HSD comprises an enclosure or housing so that the pressure and temperature of the fluid therein may be controlled.

High shear mixing devices are generally divided into three general classes, based upon their ability to mix fluids. Mixing is the process of reducing the size of particles or inhomogeneous species within the fluid. One metric for the degree or thoroughness of mixing is the energy density per unit volume that the mixing device generates to disrupt the fluid particles. The classes are distinguished based on delivered energy densities. Three classes of industrial mixers having sufficient energy density to consistently produce mixtures or emulsions with particle sizes in the range of submicron to 50 microns include homogenization valve systems, colloid mills and high speed mixers. In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average particle sizes in the submicron to about 1 micron range.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between the low energy devices and homogenization valve systems, in terms of the mixing energy density delivered to the fluid, are colloid mills and other high speed rotor-stator devices, which are classified as intermediate energy devices. A typical colloid mill configuration includes a conical or disk rotor that is separated from a complementary, liquid-cooled stator by a closely-controlled rotor-stator gap, which is commonly between 0.025 mm to 10 mm (0.001-0.40 inch). Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1 to 25 microns in the processed fluid. These capabilities render colloid mills appropriate for a variety of applications including colloid and oil/water-based emulsion processing such as that required for cosmetics, mayonnaise, or silicone/silver amalgam formation, to roofing-tar mixing.

The HSD comprises at least one revolving element that creates the mechanical force applied to the reactants therein. The HSD comprises at least one stator and at least one rotor separated by a clearance. For example, the rotors can be conical or disk shaped and can be separated from a complementarily-shaped stator. In embodiments, both the rotor and stator comprise a plurality of circumferentially-spaced rings having complementarily-shaped tips. A ring may comprise a solitary surface or tip encircling the rotor or the stator. In embodiments, both the rotor and stator comprise more than 2 circumferentially-spaced rings, more than 3 rings, or more than 4 rings. For example, in embodiments, each of three generators comprises a rotor and stator each having 3 complementary rings, whereby the material processed passes through 9 shear gaps or stages upon traversing HSD 40. Alternatively, each of three generators may comprise four rings, whereby the processed material passes through 12 shear gaps or stages upon passing through HSD 40. In some embodiments, the stator(s) are adjustable to obtain the desired shear gap between the rotor and the stator of each generator (rotor/stator set). Each generator may be driven by any suitable drive system configured for providing the desired rotation.

In some embodiments, HSD 40 comprises a single stage dispersing chamber (i.e., a single rotor/stator combination; a single high shear generator). In some embodiments, HSD 40 is a multiple stage inline disperser and comprises a plurality of generators. In certain embodiments, HSD 40 comprises at least two generators. In other embodiments, HSD 40 comprises at least 3 generators. In some embodiments, HSD 40 is a multistage mixer whereby the shear rate (which varies proportionately with tip speed and inversely with rotor/stator gap width) varies with longitudinal position along the flow pathway, as further described hereinbelow.

According to this disclosure, at least one surface within HSD 40 may be made of, impregnated with, or coated with a heterogeneous oxidation catalyst (described further hereinbelow) that is suitable for oxidizing the dicarboxylic acid precursor, as described in U.S. patent application Ser. No. 12/476,415, which is hereby incorporated herein by reference for all purposes not contrary to this disclosure.

In some embodiments, the minimum clearance (shear gap width) between the stator and the rotor is in the range of from about 0.025 mm (0.001 inch) to about 3 mm (0.125 inch). The shear gap may be in the range of from about 5 micrometers (0.0002 inch) and about 4 mm (0.016 inch). In embodiments, the shear gap is in the range of 5, 4, 3, 2 or 1 µm. In some embodiments, the minimum clearance (shear gap width) between the stator and the rotor is in the range of from about 1 µm (0.00004 inch) to about 3 mm (0.012 inch). In some embodiments, the minimum clearance (shear gap width) between the stator and the rotor is less than about 10 µm (0.0004 inch), less than about 50 µm (0.002 inch), less than about 100 µm (0.004 inch), less than about 200 µm (0.008 inch), less than about 400 µm (0.016 inch). In certain embodiments, the minimum clearance (shear gap width) between the stator and rotor is about 1.5 mm (0.06 inch). In certain embodiments, the minimum clearance (shear gap width) between the stator and rotor is about 0.2 mm (0.008 inch). In certain configurations, the minimum clearance (shear gap) between the rotor and stator is at least 1.7 mm (0.07 inch). The shear rate produced by the HSD may vary with longitudinal position along the flow pathway. In some embodiments, the rotor is set to rotate at a speed commensurate with the diameter of the rotor and the desired tip speed. In some embodiments, the HSD has a fixed clearance (shear gap width) between the stator and rotor. Alternatively, the HSD has adjustable clearance (shear gap width).

Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance transcribed by the rotor tip, $2\pi R$, where R is the radius of the rotor (meters, for example) times the frequency of revolution (for example revolutions per minute, rpm). The frequency of revolution may be greater than 250 rpm, greater than 500 rpm, greater than 1000 rpm, greater than 5000 rpm, greater than 7500 rpm, greater than 10,000 rpm, greater than 13,000 rpm, or greater than 15,000 rpm. The rotational frequency, flow rate, and temperature may be adjusted to get a desired product profile. If channeling should occur, and reaction is inadequate, the rotational frequency may be increased to minimize undesirable channeling. Alternatively or additionally, oxidation product may be introduced into a second or subsequent HSD 40.

HSD 40 may provide a tip speed in excess of 22.9 m/s (4500 ft/min) and may exceed 40 m/s (7900 ft/min), 50 m/s (9800 ft/min), 100 m/s (19,600 ft/min), 150 m/s (29,500 ft/min), 200 m/s (39,300 ft/min), or even 225 m/s (44,300 ft/min) or greater in certain applications. For the purpose of this disclosure, the term 'high shear' refers to mechanical rotor stator devices (e.g., colloid mills or rotor-stator dispersers) that are capable of tip speeds in excess of 5.1 m/s (1000 ft/min) or those values provided herein and require an external mechanically driven power device to drive energy into the stream of products to be reacted. By contacting the reactants with the rotating members, which can be made from, coated with, or impregnated with stationary catalyst, significant energy is transferred to the reaction. The energy consumption of the HSD 40 will generally be very low.

In some embodiments, HSD 40 is capable of delivering at least 300 L/h at a tip speed of at least 22.9 m/s (4500 ft/min). The power consumption may be about 1.5 kW. HSD 40 combines high tip speed with a very small shear gap to produce significant shear on the material being processed. The amount of shear will be dependent on the viscosity of the fluid in HSD 40. Accordingly, a local region of elevated pressure and temperature is created at the tip of the rotor during operation of HSD 40. In some cases the locally elevated pressure is about 1034.2 MPa (150,000 psi). In some cases the locally elevated temperature is about 500° C. In some cases, these local pressure and temperature elevations may persist for nano- or pico-seconds.

An approximation of energy input into the fluid (kW/L/min) can be estimated by measuring the motor energy (kW) and fluid output (L/min). As mentioned above, tip speed is the velocity (ft/min or m/s) associated with the end of the one or more revolving elements that is creating the mechanical force applied to the fluid. In embodiments, the energy expenditure is at least about 1000 W/m$^3$, 5000 W/m$^3$, 7500 W/m$^3$, 1 kW/m$^3$, 500 kW/m$^3$, 1000 kW/m$^3$, 5000 kW/m$^3$, 7500 kW/m$^3$, or greater. In embodiments, the energy expenditure of HSD 40 is greater than 1000 watts per cubic meter of fluid therein. In embodiments, the energy expenditure of HSD 40 is in the range of from about 3000 W/m$^3$ to about 7500 kW/m$^3$. In embodiments, the energy expenditure of HSD 40 is in the range of from about 3000 W/m$^3$ to about 7500 W/m$^3$. The actual energy input needed is a function of what reactions are occurring within the HSD, for example, endothermic and/or exothermic reaction(s), as well as the mechanical energy required for dispersing and mixing feedstock materials. In some applications, the degree of exothermic reaction(s) (e.g. oxidation) occurring within the HSD mitigates some or substantially all of the reaction energy needed from the motor input. When dispersing a gas in a liquid, the energy requirements are significantly less than when all reactants are liquid.

The shear rate is the tip speed divided by the shear gap width (minimal clearance between the rotor and stator). The shear rate generated in HSD 40 may be in the greater than 20,000 s$^{-1}$. In some embodiments the shear rate is at least 30,000 s$^{-1}$ or at least 40,000 s$^{-1}$. In some embodiments the shear rate is greater than 30,000 s$^{-1}$. In some embodiments the shear rate is at least 100,000 s$^{-1}$. In some embodiments the shear rate is at least 500,000 s$^{-1}$. In some embodiments the shear rate is at least 1,000,000 s$^{-1}$. In some embodiments the shear rate is at least 1,600,000 s$^{-1}$. In some embodiments the shear rate is at least 3,000,000 s$^{-1}$. In some embodiments the shear rate is at least 5,000,000 s$^{-1}$. In some embodiments the shear rate is at least 7,000,000 s$^{-1}$. In some embodiments the shear rate is at least 9,000,000 s$^{-1}$. In embodiments where the rotor has a larger diameter, the shear rate may exceed about 9,000,000 s$^{-1}$. In embodiments, the shear rate generated by HSD 40 is in the range of from 20,000 s$^{-1}$ to 10,000,000 s$^{-1}$. For example, in one application the rotor tip speed is about 40 m/s (7900 ft/min) and the shear gap width is 0.0254 mm (0.001 inch), producing a shear rate of 1,600,000 s$^{-1}$. In another application the rotor tip speed is about 22.9 m/s (4500 ft/min) and the shear gap width is 0.0254 mm (0.001 inch), producing a shear rate of about 901,600 s$^{-1}$.

In some embodiments, HSD 40 comprises a colloid mill. Suitable colloidal mills are manufactured by IKA® Works, Inc. Wilmington, N.C. and APV North America, Inc. Wilmington, Mass., for example. In some instances, HSD 40 comprises the DISPAX REACTOR® of IKA® Works, Inc.

In some embodiments, each stage of the external HSD has interchangeable mixing tools, offering flexibility. For example, the DR 2000/4 DISPAX REACTOR® of IKA® Works, Inc. Wilmington, N.C. and APV North America, Inc. Wilmington, Mass., comprises a three stage dispersing module. This module may comprise up to three rotor/stator combinations (generators), with choice of fine, medium, coarse, and super-fine for each stage. This allows for variance of shear rate along the direction of flow. In some embodiments, each of the stages is operated with super-fine generator.

Figure 3:
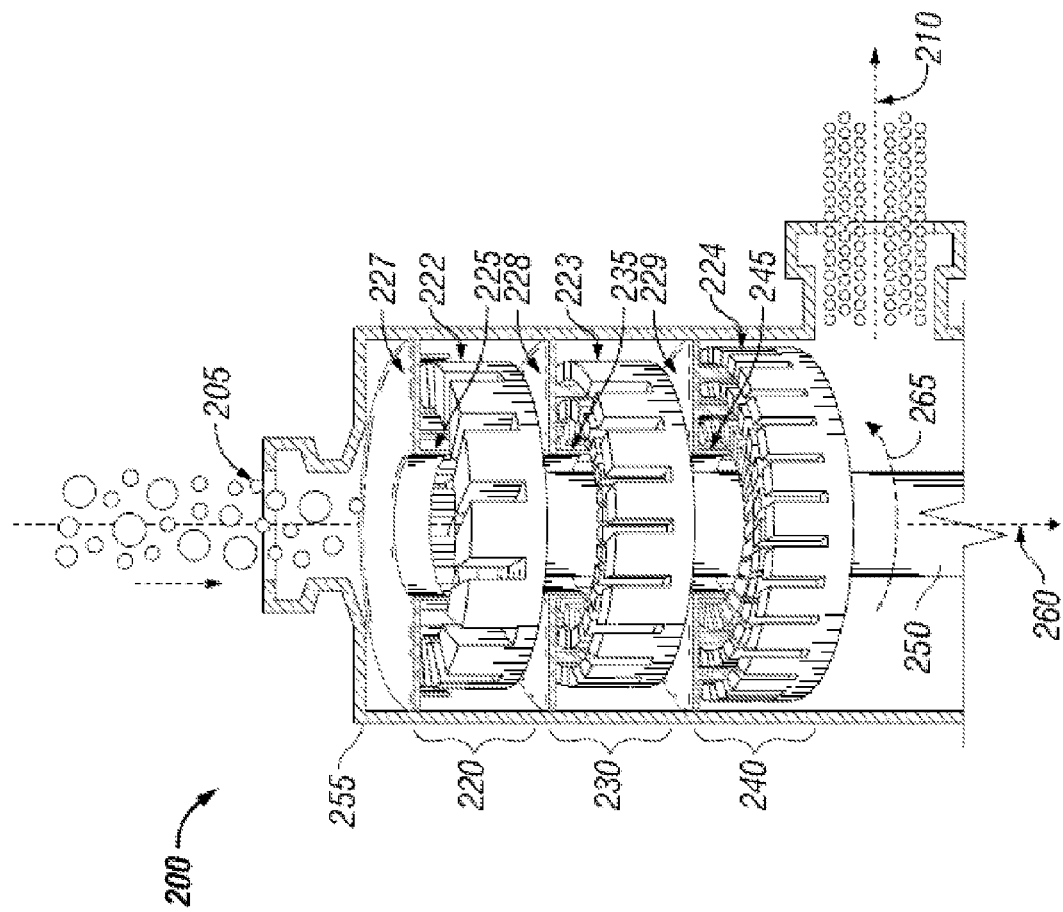
FIG. 3 is a longitudinal cross-section view of a high shear mixing device suitable for use in embodiments of the disclosed system.

In embodiments, a scaled-up version of the DISPAX® reactor is utilized. For example, in embodiments HSD 40 comprises a SUPER DISPAX REACTOR® DRS 2000. The HSD unit may be a DR 2000/50 unit, having a flow capacity of 125,000 liters per hour, or a DRS 2000/50 having a flow capacity of 40,000 liters/hour. Because residence time is increased in the DRS unit, the fluid therein is subjected to more shear. Referring now to FIG. 3, there is presented a longitudinal cross-section of a suitable device HSD 200 for use as HSD 40. HSD 200 of FIG. 3 is a dispersing device comprising three stages or rotor-stator combinations, 220, 230, and 240. The rotor-stator combinations may be known as generators 220, 230, 240 or stages without limitation. Three rotor/stator sets or generators 220, 230, and 240 are aligned in series along drive shaft 250.

First generator 220 comprises rotor 222 and stator 227. Second generator 230 comprises rotor 223, and stator 228. Third generator 240 comprises rotor 224 and stator 229. For each generator the rotor is rotatably driven by input 250 and rotates about axis 260 as indicated by arrow 265. The direction of rotation may be opposite that shown by arrow 265 (e.g., clockwise or counterclockwise about axis of rotation 260). Stators 227, 228, and 229 may be fixably coupled to the wall 255 of HSD 200. As mentioned hereinabove, each rotor and stator may comprise rings of complementarily-shaped tips, leading to several shear gaps within each generator.

As mentioned hereinabove, each generator has a shear gap width which is the minimum distance between the rotor and the stator. In the embodiment of FIG. 3, first generator 220 comprises a first shear gap 225; second generator 230 comprises a second shear gap 235; and third generator 240 comprises a third shear gap 245. In embodiments, shear gaps 225, 235, 245 have widths in the range of from about 0.025 mm to about 10 mm. Alternatively, the process comprises utilization of an HSD 200 wherein the gaps 225, 235, 245 have a width in the range of from about 0.5 mm to about 2.5 mm. In certain instances the shear gap width is maintained at about 1.5 mm. Alternatively, the width of shear gaps 225, 235, 245 are different for generators 220, 230, 240. In certain instances, the width of shear gap 225 of first generator 220 is greater than the width of shear gap 235 of second generator 230, which is in turn greater than the width of shear gap 245 of third generator 240. As mentioned above, the generators of each stage may be interchangeable, offering flexibility. HSD 200 may be configured so that the shear rate remains the same or increases or decreases stepwise longitudinally along the direction of the flow 260.

Generators 220, 230, and 240 may comprise a coarse, medium, fine, and super-fine characterization, having different numbers of complementary rings or stages on the rotors and complementary stators. Rotors 222, 223, and 224 and stators 227, 228, and 229 may be toothed designs. Each generator may comprise two or more sets of complementary rotor-stator rings. In embodiments, rotors 222, 223, and 224 comprise more than 3 sets of complementary rotor/stator rings.

HSD 40 may be a large or small scale device. In embodiments, system 100/100A is used to process from less than 100 gallons per minute to over 5000 gallons per minute. In embodiments, one or more HSD 40 processes at least 100, 500, 750, 900, 1000, 2000, 3000, 4000, 5000 gpm or more. Large scale units may produce 1000 gal/h (24 barrels/h). The inner diameter of the rotor may be any size suitable for a desired application. In embodiments, the inner diameter of the rotor is from about 12 cm (4 inch) to about 40 cm (15 inch). In embodiments, the diameter of the rotor is about 6 cm (2.4 inch). In embodiments, the outer diameter of the stator is about 15 cm (5.9 inch). In embodiments, the diameter of the stator is about 6.4 cm (2.5 inch). In some embodiments the rotors are 6.0 cm (2.4 inch) and the stators are 6.4 cm (2.5 inch) in diameter, providing a clearance of about 4 mm. In certain embodiments, each of three stages is operated with a super-fine generator comprising a number of sets of complementary rotor/stator rings.

In some embodiments, high shear device 200 comprises at least one catalytic surface in any of the rotor/stator stages. In some cases, the catalytic surface is constructed to be part of a rotor. In some cases, the catalytic surface is constructed to be part of a stator. In some cases, the catalytic surface is constructed to be part of a rotor and a stator. When a reactant mixture is introduced into shear device 200, a catalytic reaction is induced when the mixture comes in touch with the catalytic surface. In some embodiments, the HSD comprises a catalytic surface made of a suitable oxidation catalyst that promotes the oxidation reactions to form dicarboxylic acid. In some cases, vessel 10 is omitted. In some other cases, vessel 10 is used in conjunction with HSD comprising such catalytic surface.

Figure 2:
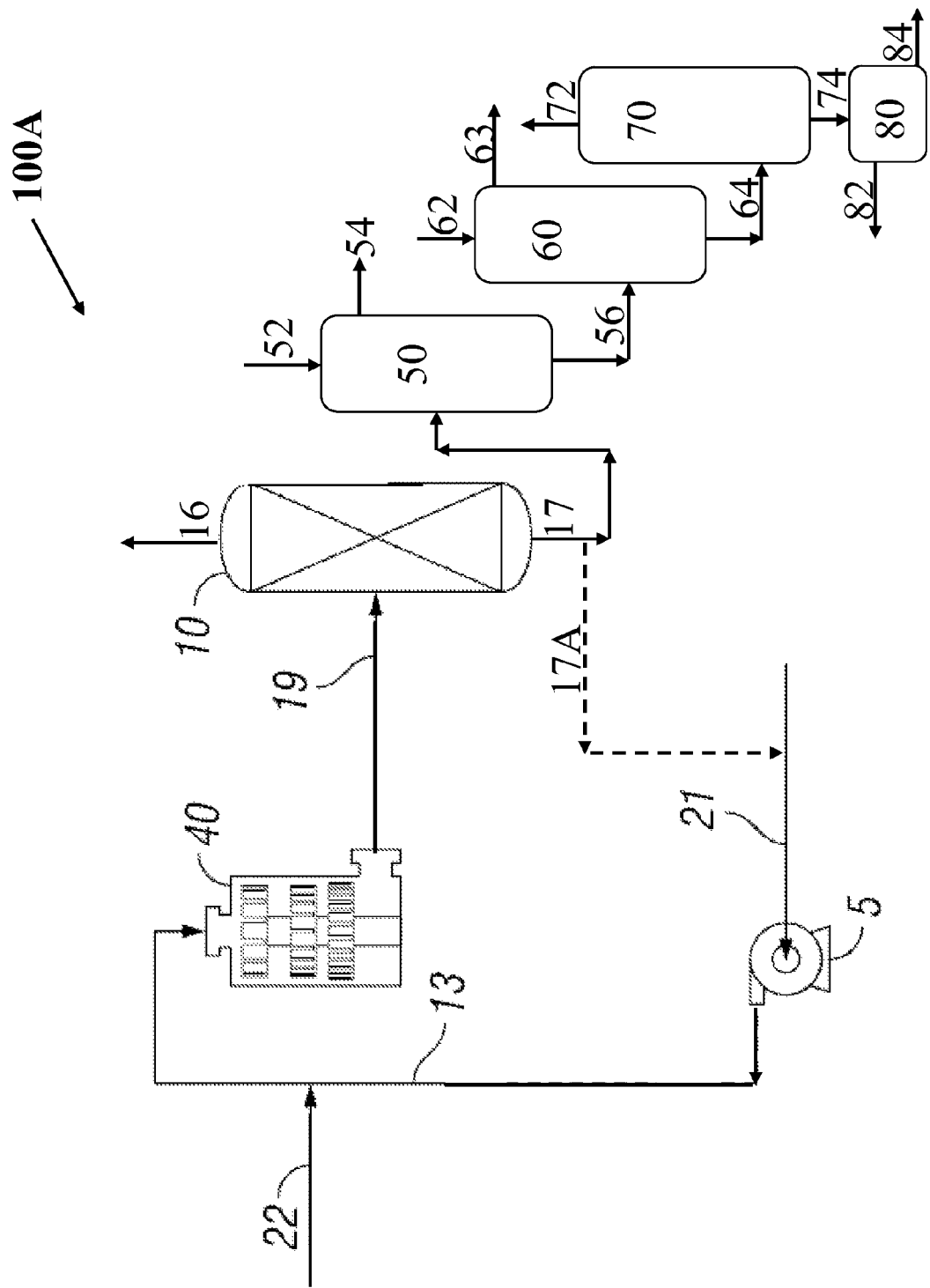
FIG. 2 is a schematic of a high shear system comprising an external high shear mixer/disperser according to another embodiment of the present disclosure.

HSD 200 is configured for receiving at inlet 205 a fluid mixture, e.g., from line 13 in FIG. 1. The mixture comprises oxidant and dicarboxylic acid precursor (e.g. TAP) as reactants. Feed stream entering inlet 205 is pumped serially through generators 220, 230, and then 240, such that an emulsion is produced. Product exits HSD 200 via outlet 210 (and line 19 of FIGS. 1 and 2). The rotors 222, 223, 224 of each generator rotate at high speed relative to the fixed stators 227, 228, 229, providing a high shear rate. The rotation of the rotors pumps fluid, such as the feed stream entering inlet 205, outwardly through the shear gaps (and, if present, through the spaces between the rotor teeth and the spaces between the stator teeth), creating a localized high shear condition. High shear forces exerted on fluid in shear gaps 225, 235, and 245 (and, when present, in the gaps between the rotor teeth and the stator teeth) through which fluid flows process the fluid and create high shear product. The product comprises a high shear mixture (e.g. a dispersion) of oxidant in feed mixture. Product exits HSD 200 via high shear outlet 210 (line 19 of FIGS. 1 and 2).

Without wishing to be limited by theory, it is believed that the high shear product at 210 may comprise an abundance of free radicals. The shear provided by the high velocity may generate numerous micronized or submicronized globules. The high velocity, associated surface phenomenon and other dissociating forces may generate the free radicals in the product. This high shear-treated product is highly reactive and may remain in a reactive state for substantial time periods, e.g. 30 minutes or more in some instances, even upon exiting the HSD.

As mentioned above, in certain instances, HSD 200 comprises a DISPAX REACTOR® of IKA® Works, Inc. Wilmington, N.C. and APV North America, Inc. Wilmington, Mass. Several models are available having various inlet/outlet connections, horsepower, tip speeds, output rpm, and flow rate. Selection of the HSD will depend on throughput selection, for example. IKA® model DR 2000/4, for example, comprises a belt drive, 4M generator, PTFE sealing ring, inlet flange 25.4 mm (1 inch) sanitary clamp, outlet flange 19 mm (¾ inch) sanitary clamp, 2HP power, output speed of 7900 rpm, flow capacity (water) approximately 300-700 L/h (depending on generator), a tip speed of from 9.4-41 m/s (1850 ft/min to 8070 ft/min). Scale up may be performed by using a plurality of HSDs, or by utilizing larger HSDs. Scale-up using larger models is readily performed, and results from larger HSD units may provide improved efficiency in some instances relative to the efficiency of lab-scale devices. The large scale unit may be a DISPAX® 2000/unit. For example, the DRS 2000/5 unit has an inlet size of 51 mm (2 inches) and an outlet of 38 mm (1.5 inches).

In embodiments HSD 40 or portions thereof are manufactured from refractory/corrosion resistant materials. For example, sintered metals, INCONEL® alloys, HASTELLOY® materials may be used. For example, when the mixture is caustic the rotors, stators, and/or other components of HSD 40 may be manufactured of refractory materials (e.g. sintered metal) in various applications.

Vessel 10. High shear dicarboxylic acid production system 100/100A comprises vessel 10. Vessel 10 is operable to separate vapor comprising vaporized medium (e.g., vaporized aqueous acetic acid), and oxygen-depleted gas from oxidation product comprising dicarboxylic (e.g. terephthalic) acid. The oxygen-depleted gas may comprise, for example, carbon dioxide, methane, inert components, unreacted oxygen, or a combination thereof. Gas/vapor may be extracted from vessel 10 via vessel 10 outlet gas line 16. Oxidation product comprising terephthalic acid may be extracted from vessel 10 via vessel 10 oxidation product outlet line 17.

Vessel 10 may be operable continuously, semi-continuously, or batchwise. Vessel 10 may comprise one or more unit(s) configured in series or in parallel. For parallel operation, outlet line 19 may divide to introduce high shear-treated oxidation product comprising terephthalic acid into multiple vessels 10.

Vessel(s) may include one or more of the following components: heating and/or cooling capabilities, pressure measurement instrumentation, temperature measurement instrumentation, one or more injection points, and level regulator, as are known in the art of vessel design. For example, a heating and/or cooling apparatus may comprise, for example, a heat exchanger. As the oxidation may be exothermic (e.g. production of terephthalic acid by the oxidation of a TAP is highly exothermic), vessel 10 may comprise a heat exchanger whereby the temperature within vessel 10 may be maintained at a desired temperature, as known in the art.

Heat Transfer Devices. Internal or external heat transfer devices are also contemplated in variations of the system. For example, the reactants may be preheated via any method known to one skilled in the art. Some suitable locations for one or more such heat transfer devices are upstream of pump 5, between pump 5 and HSD 40, between HSD 40 and flow line 19, and within or between vessel 10 and downstream purification apparatus 50, 60, 70, and/or 80. Some non-limiting examples of such heat transfer devices are shell, tube, plate, and coil heat exchangers, as are known in the art. HSD 40/200 may comprise an inner shaft which may be cooled, for example water-cooled, to partially or completely control the temperature within the HSD.

Pumps. High shear TAPS 100 may comprise pump 5. Pump 5 is configured for either continuous or semi-continuous operation, and may be any suitable pumping device that is capable of providing controlled flow through HSD 40 and system 100. In applications pump 5 provides greater than 202.65 kPa (2 atm) pressure or greater than 303.97 kPa (3 atm) pressure. Pump 5 may be a Roper Type 1 gear pump, Roper Pump Company (Commerce Georgia) Dayton Pressure Booster Pump Model 2P372E, Dayton Electric Co (Niles, Ill.) is one suitable pump. Preferably, all contact parts of the pump comprise stainless steel, for example, 316 stainless steel. In some embodiments of the system, pump 5 is capable of pressures greater than about 2026.5 kPa (20 atm). In addition to pump 5, one or more additional, high pressure pumps may be included in the systems illustrated in FIGS. 1 and 2. For example, a booster pump, which may be similar to pump 5, may be included between HSD 40 and flow line 19.

Separation Apparatus 50. A high shear terephthalic acid production system according to this disclosure may further comprise separation apparatus 50. In embodiments, separation apparatus 50 is any separator suitable for separating oxidation product comprising TA from the non-aqueous component (e.g. the monocarboxylic acid such as acetic acid) of the liquid medium. Separation apparatus 50 may be operable to replace the carboxylic acid medium of the high shear oxidation product comprising TA with water, to facilitate downstream hydrogenation. Separation apparatus 50 may thus comprise apparatus for separating liquid from terephthalic acid crystals and subsequently dissolving the separated TA in water. Separation apparatus 50 may be selected from centrifugal separators, filtration separators, and mother-liquor displacement apparatus, as known in the art. Separation apparatus 50 may comprise one or more centrifuges, filtration units, and/or evaporators (e.g. flash evaporators) operable to separate crude TA from the oxidation product in line 19 or 17 and one or more mixing units operable to form an aqueous slurry of the separated TA. In embodiments, separation apparatus 50 comprises a solid bowl-type centrifugal separator. In embodiments, separator 50 comprises a rotary vacuum filter. In embodiments, separation apparatus 50 comprises mother-liquor displacement apparatus as described in U.S. Patent App. No. 2007/0015935, which is hereby incorporated herein in its entirety for all purposes not contrary to this disclosure. Separation apparatus 50 may further comprise a dryer and/or a washing unit, whereby separated crystals of acid are washed. Separation apparatus may comprise an inlet line 52 whereby water is introduced and separated and/or dried solid crystals of crude TA are redissolved in water. Heating may be incorporated within separation apparatus 50 to dissolve the separated crystals (comprising dicarboxylic acid and co-crystallized impurities) in the water and provide an aqueous solution. Aqueous solution comprising terephthalic acid and any impurities which were separated therewith exits separation apparatus 50 via separated product outlet line (also referred to herein as aqueous slurry outlet line) 56. One or more reaction medium outlet lines 54 may be configured for removal of separated medium from separation apparatus 50.

Hydrogenation Apparatus 60. The high shear dicarboxylic acid production system may further comprise hydrogenation apparatus 60. Hydrogenation apparatus 60 may be any apparatus known in the art for hydrogenating an aqueous solution of TA to hydrogenate impurities, e.g. to convert 4-CBA to p-toluic acid and convert color bodies to colorless compounds. Hydrogenation apparatus 60 is operable to contact an aqueous slurry comprising crude TA and impurities with hydrogen in the presence of a heterogeneous catalyst. Hydrogenation apparatus 60 may contain a bed of catalyst. The hydrogenation catalyst may comprise, for example, a noble metal such as palladium on a suitable support, such as a carbon support. One or more gas inlet lines 62 are configured for introduction of hydrogen into hydrogenation apparatus 60.

In embodiments, hydrogenation apparatus 60 comprises a HSD. In such embodiments, the hydrogenation HSD is configured for introduction of hydrogen and aqueous dicarboxylic acid solution thereto such that conversion of 4-CBA to p-toluic acid occurs. Hydrogenation catalyst may be introduced into the hydrogenation HSD along with the aqueous solution, or, in instances, a contact surface (e.g., a rotor and/or a stator) within the hydrogenation HSD may comprise or contain thereon suitable hydrogenation catalyst, as discussed hereinabove with regard to oxidation catalyst.

Crystallization Apparatus 70. The high shear dicarboxylic acid production system may further comprise crystallization apparatus 70. Crystallization apparatus 60 may be fluidly connected with hydrogenation apparatus 60 via hydrogenation product outlet line 64. Crystallization apparatus 70 may be any apparatus known in the art to be suitable for forming crystals of the desired dicarboxylic acid. Crystallization apparatus 70 may be configured for a staged equilibrium crystallization approach, as known in the art. With such an approach, evaporation is controlled against back pressure regulation in multiple crystallizer stages to control the rate at which the hydrogenation product stream exiting hydrogenation apparatus 60 via hydrogenation product outlet line 64 is crystallized. For TA, shock cooling of hydrogenation product to temperatures below 165° C. may promote co-precipitation (co-crystallization) of impurities, especially p-toluic acid, which is an undesirable contaminant. Staged cooling may minimize such undesirable co-crystallization. As described in U.S. Pat. No. 3,931,305, the impurity concentration in the TA is affected by the lowest temperature to which the hydrogenation product is flashed. In embodiments, therefore, the majority of the PTA is crystallized at a temperature of higher than about 160° C. to about 182° C., which is a threshold temperature at which substantial undesirable p-toluic acid co-crystallization occurs. One or more lines 72 may be configured for removal of evaporated solvent from crystallization apparatus 70.

Solid/Liquid Separator 80. The high shear dicarboxylic acid production system may further comprise solid/liquid separator 80. Solid/liquid separator 80 is any separator known in the art to be operable to separate crystals of dicarboxylic acid produced in crystallization apparatus 70 from aqueous medium. Crystallization apparatus 70 outlet line 74 is configured to introduce aqueous solution comprising precipitated crystals of PTA and water into solid/liquid separator 80. Solid/liquid separator 80 comprises a liquids outlet line 82 for removal of aqueous solution and a purified dicarboxylic acid (e.g. a PTA) product outlet line 84 for removal of solid crystals of purified dicarboxylic acid from solid/liquid separator 80. Solid/liquid separator 80 may comprise a centrifuge, a filtration unit, a settler, or a combination thereof.

Figure 4:
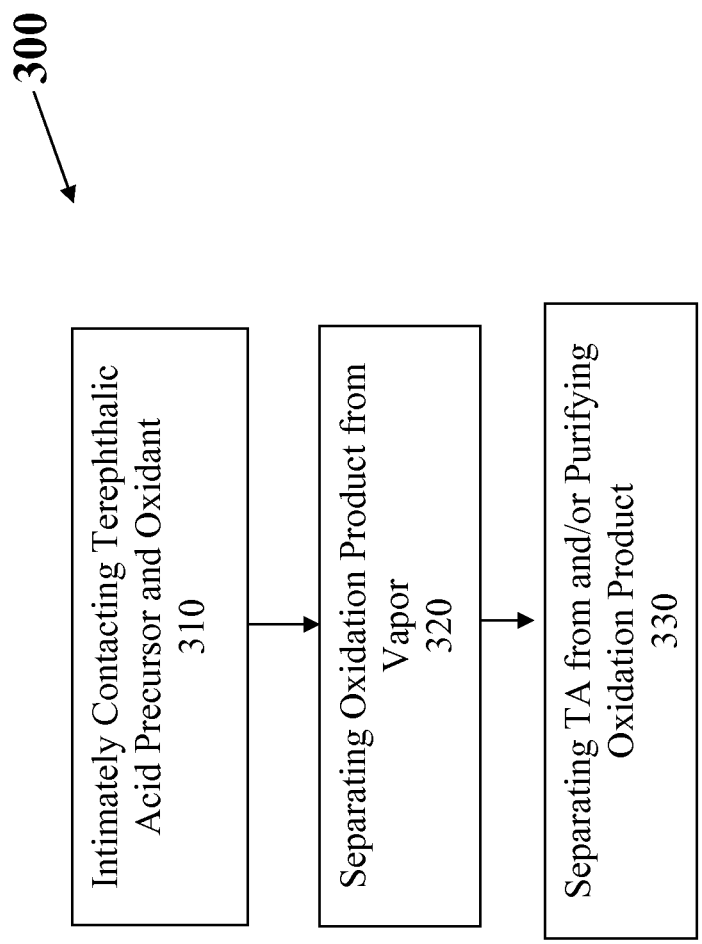
FIG. 4 is a box flow diagram of a method of producing purified terephthalic acid (PTA) according to an embodiment of this disclosure.

High Shear Method for Producing Dicarboxylic Acid. A method of producing dicarboxylic acid via high shear oxidation of dicarboxylic acid precursor will now be described with respect to FIG. 4 which is a schematic of a method 300 of producing purified dicarboxylic acid according to an embodiment of this disclosure. Once again, although description will be made with reference to terephthalic acid production, it is to be understood that the method is suitable for the production of a variety of dicarboxylic acids. Method 300 comprises intimately contacting terephthalic acid precursor and oxidant at 310 and separating oxidation product comprising TA from vapor at 320. Method 300 may further comprise separating terephthalic acid from the oxidation product and/or further purifying the oxidation product at 330.

Intimately Contacting Terephthalic Acid Precursor and Oxidant 310. High shear terephthalic acid production method 300 comprises intimately contacting terephthalic acid precursor and oxidant at 310. Intimately mixing at 310 comprises subjecting the feed mixture comprising TAP to high shear in the presence of oxidant to produce a high shear-treated stream. The high shear treated stream exiting HSD 40 via line 19 may be in the form of a dispersion of oxidant in the feed mixture. In embodiments, subjecting the feed mixture to high shear comprises subjecting to a shear rate of at least 10,000 $s^{-1}$, at least 20,000 $s^{-1}$, at least 30,000 $s^{-1}$, or higher, as further discussed hereinbelow. In embodiments, intimately contacting the feed mixture and oxidant at 310 comprises introducing the feed mixture (e.g., via lines 21 and 13) and the oxidant (e.g., via line 22) into a HSD 40, as indicated in FIG. 1.

Referring now to FIG. 1, intimately mixing the feed mixture and oxidant at 310 may comprise introducing the feed mixture into HSD 40. Pump 5 is used to pump the feed mixture into HSD 40. Oxidant may be introduced into HSD 40 via one or more dispersible gas lines 22, may be introduced directly into HSD 40, or may be present in the feed mixture introduced via line 21. As discussed above, the oxidant may be any suitable oxygen-containing gas. In embodiments, the oxidant is selected from oxygen, oxygen-enriched air, and air. The oxidant introduced via line 22 may further comprise, an inert or diluent gas, such as carbon dioxide, which may be more soluble in the solvent than nitrogen. The diluent gas may be derived, for instance, from the vent gas produced during the oxidation reaction and extracted via vessel 10 outlet line 16. Where the diluent gas is derived from the vent gas, the vent gas may have been treated, e.g. by high temperature catalytic combustion, to convert any methyl bromide present to HBr and Br, and may be recycled, at least in part, without removing its HBr content since HBr can be employed as a catalyst component in the oxidation reaction. For example, following treatment to convert MeBr to HBr and Br, part of the vent gas may be diverted for dilution of the oxygen supply to the oxidation reaction in HSD 40 while the remainder may be processed further, e.g. for disposal or use as a fluidizing medium for conveying purposes. The diverted portion of the treated off gas may be cooled (for instance, by heat exchange with the vent gas upstream of the MeBr conversion step) and recompressed (before or after admixture with the oxygen supply) sufficiently to allow it to be reintroduced in the oxidation reaction.

Oxidant may be introduced into line 13 via line 22 or may be introduced elsewhere throughout high shear terephthalic acid production system 100. In embodiments, oxidant is introduced into line 13 via line 22. In embodiments, oxidant and feed mixture are separately introduced directly into HSD 40. The feed mixture comprises dicarboxylic acid precursor (e.g. TAP) and suitable medium. As discussed above, the medium may comprise water and one or more aliphatic monocarboxylic acids (e.g. containing 2 to 6 carbon atoms). The water content used in the conventional production of terephthalic acid by liquid phase oxidation of paraxylene is typically such that water makes up between about 3% and 20% by weight of the feed mixture comprising carboxylic acid and water supplied to the reaction zone. In embodiments, the feed mixture comprises between 3% and 10% by weight of water. In embodiments, the water content is substantially greater than that in the feed conventionally fed to the oxidation reaction zone. In embodiments, the feed mixture comprises from about 3% to about 30%, from about 10% to about 30%, from about 12% to about 30%, greater than 10%, or greater than about 12% by weight of water. In embodiments wherein the TAP comprises p-xylene, the solubility of paraxylene in the medium (e.g. acetic acid/water) decreases significantly with increasing water content, imposing limits on the amount of water that can be in the reaction mixture in conventional TA production since the medium/TAP ratios are low, typically between 4:1 and 7:1. In embodiments according to this disclosure, the feed mixture comprises medium (including water) and TAP in a ratio of from about 4:1 to about 200:1; from about 4:1 to about 150:1; from about 4:1 to about 50:1; from about 4:1 to about 7:1; greater than about 4:1; greater than about 7:1; greater than about 10:1; greater than about 20:1; greater than about 30:1; greater than about 40:1; or greater than about 50:1.

The feed mixture may further comprise an oxidation catalyst. The catalyst systems that may be employed in the oxidation process include any catalyst system conventionally used for liquid-phase oxidation of alkyl aromatic hydrocarbon(s). Due to the enhanced degree of contact provided by the HSD, oxidation catalyst may not be necessary in some embodiments or amounts of oxidation catalyst required for production of an amount of TA are reduced relative to conventional production methods. In embodiments, the feed mixture further comprises oxidation catalyst soluble in the feed mixture comprising TAP(s) and suitable medium. Alternatively or additionally, a heterogeneous catalyst may be utilized. In embodiments, the oxidation catalyst, whether homogeneous or heterogeneous comprises one or more heavy metal compounds. The heavy metal compound(s) may be selected from cobalt and manganese compounds. The catalyst may optionally include an oxidation promoter such as bromine or acetaldehyde. For example, the catalyst may take any of the forms that have been used in the liquid phase oxidation of TAPs, such as oxidation of TAP(s) in aliphatic carboxylic acid solvent(s). Examples of such catalysts include, but are not limited to, bromides, bromoalkanoates and alkanoates (typically C1-C4 alkanoates such as acetates) of cobalt and/or manganese. Compounds of other heavy metals such as vanadium, molybdenum, iron, chromium, lanthanides such as cerium, hafnium, zirconium and/or nickel may be used instead of or in addition to cobalt and/or manganese. A suitable catalyst system comprises a mixture of cobalt, manganese and bromine compounds or complexes. In embodiments, such compounds or complexes are soluble in aqueous acetic acid. In embodiments, the atomic ratio of Co:Mn:Br in the catalyst system is in the range of from about 5-40:1.0:4-40, or from about 16-40:1.0:10-40. The catalyst may include manganese bromide ($MnBr_2$). The catalyst may alternatively or additionally include one or more noble metals or compounds thereof, for example, palladium and/or platinum or compounds thereof. The catalyst may be in a highly divided form. The catalyst system may further comprise an oxidation promoter. The oxidation promoter may be selected from elemental bromine, ionic bromide (e.g. HBr, NaBr, KBr, $NH_4Br$) and/or organic bromide (e.g. bromobenzenes, mono- and di-bromoacetic acid, benzyl-bromide, tetrabromomethane, ethylene-di-bromide, bromoacetyl bromide, etc.). In embodiments, the oxidation promoter is selected from ketones, including but not limited to, methylethyl ketone, and/or aldehydes, including, but not limited to, acetaldehyde.

In embodiments, the oxidation catalyst is in heterogeneous form. The heterogeneous catalyst may be supported as known in the art, for example, alpha alumina, spinel, and mullite, silica, alumina, titania, zirconia and combinations thereof. In embodiments, the heterogeneous catalyst is coated on a contact surface of HSD 40, as discussed hereinabove.

Referring now to FIG. 1, when present, pump 5 may be operated to pump the feed mixture through line 13, and to build pressure and feed HSD 40, providing a controlled flow throughout high shear (HSD) 40 and high shear system 100/100A. In some embodiments, pump 5 increases the pressure of the HSD inlet stream in line 13 to greater than 200 kPa (2 atm) or greater than about 300 kPa (3 atmospheres). In this way, high shear system 100 may combine high shear with pressure to enhance production of dicarboxylic acid.

Within high shear device 40, TAP is intimately mixed with oxidant. The temperature, shear rate and/or residence time within HSD 40 may be controlled to effect desired oxidation and provide a sufficient but not excessive amount of oxidant.

Subjecting the feed mixture and oxidant to high shear may produce a dispersion comprising oxidant dispersed throughout a liquid phase comprising feed mixture. In embodiments, a dispersion comprising nanobubbles and/or microbubbles of the oxidant is formed. In embodiments, the bubbles in the dispersion have an average diameter of less than or about 5, 4, 3, 2 or 1 μm. In embodiments, the bubbles in the dispersion have an average particle diameter in the nanometer range, the micron range, or the submicron range.

In an exemplary embodiment, the high shear device comprises a commercial disperser such as IKA® model DR 2000/4, a high shear, three stage dispersing device configured with three rotors in combination with stators, aligned in series, as described above. The disperser is operated to subject the contents to high shear. The rotor/stator sets may be configured as illustrated in FIG. 3, for example. In such an embodiment, the feed enters the high shear device via line 13 and enter a first stage rotor/stator combination having circumferentially spaced first stage shear openings. The coarse mixture exiting the first stage enters the second rotor/stator stage, which has second stage shear openings. The mixture emerging from the second stage enters the third stage rotor/stator combination having third stage shear openings. The rotors and stators of the generators may have circumferentially spaced complementarily-shaped rings. A high shear-treated product exits the high shear device via outlet 210 (line 19 in FIGS. 1 and 2).

In some embodiments, the shear rate increases stepwise longitudinally along the direction of the flow 260, or going from an inner set of rings of one generator to an outer set of rings of the same generator. In other embodiments, the shear rate decreases stepwise longitudinally along the direction of the flow, 260, or going from an inner set of rings of one generator to an outer set of rings of the same generator (outward from axis 200). For example, in some embodiments, the shear rate in the first rotor/stator stage is greater than the shear rate in subsequent stage(s). For example, in some embodiments, the shear rate in the first rotor/stator stage is greater than or less than the shear rate in a subsequent stage(s). In other embodiments, the shear rate is substantially constant along the direction of the flow, with the stage or stages being the same. If HSD 40 includes a PTFE seal, for example, the seal may be cooled using any suitable technique that is known in the art. The HSD 40 may comprise a shaft in the center which may be used to control the temperature within HSD 40.

The rotor(s) of HSD 40 may be set to rotate at a speed commensurate with the diameter of the rotor and the desired tip speed. As described above, the HSD (e.g., colloid mill or toothed rim disperser) has either a fixed clearance between the stator and rotor or has adjustable clearance.

In some embodiments, HSD 40 delivers at least 300 L/h at a nominal tip speed of at least 22 m/s (4500 ft/min), 40 m/s (7900 ft/min), and which may exceed 225 m/s (45,000 ft/min) or greater. The power consumption may be about 1.5 kW or higher as desired. Although measurement of instantaneous temperature and pressure at the tip of a rotating shear unit or revolving element in HSD 40 is difficult, it is estimated that the localized temperature seen by the intimately mixed reactants may be in excess of 500° C. and at pressures in excess of 500 kg/cm$^2$ under high shear conditions.

Conditions of temperature, pressure, space velocity, oxidant selection, and/or ratio of oxidant to TAP may be adjusted to effect substantially complete oxidation of TAP and minimal production of undesirable partial oxidation contaminants (e.g., partial oxidation products CBA and p-toluic acid typically formed during catalytic oxidation of paraxylene). The global temperature for oxidation and/or the temperature of the feed mixture introduced into HSD 40 is sufficiently high to ensure that the reaction is initiated but not so high that the temperature rise during exothermic oxidation leads to a temperature which results in excessive burning of solvent and/or aromatics. In embodiments, the temperature of the material introduced into HSD 40 is in the range of from about 80° C. to about 200° C., between about 120° C. and 180° C., or between about 140° C. and 170° C. In embodiments, the global operating temperature within HSD 40 is a temperature of less than about 200° C., less than about 180° C., or less than about 160° C. In embodiments, the global temperature is ambient temperature. In embodiments, the global operating temperature is room temperature. Without wishing to be limited by theory, it is believed that the conditions within HSD 40 may enable or force reactions that would otherwise not be thermodynamically favorable under the operating conditions utilized therein. For example, the oxidation may occur at temperatures less than the conventional oxidation temperature. Also, the use of HSD 40 may minimize the extent of undesired reactions, such as the production of partial oxidation products, and/or minimize the amount of unreacted oxidant that exits the oxidation zone (i.e., that exits HSD 40). The temperature of the high shear product stream comprising dicarboxylic acid emerging from HSD 40 will generally be greater than the inlet temperature. The temperature of the high shear product dispersion exiting HSD 40 via high shear-treated product outlet line 19 may be between about 180° C. and about 250° C., between about 180° C. and about 230° C., or between about 190° C. and about 220° C.

The high shear oxidation presented herein requires much less contact time between oxidant and TAP which may enhance throughput; the effectiveness of oxidation may minimize the number of partial oxidation contaminants in the high shear product, minimizing the number and/or extent of downstream purification steps. The residence time within HSD 40 is typically low. For example, the residence time can be in the millisecond range, can be about 10, 20, 30, 40, 50, 60, 70, 80, 90 or about 100 milliseconds, can be about 100, 200, 300, 400, 500, 600, 700, 800, or about 900 milliseconds, can be in the range of seconds, or can be any range thereamong.

As mentioned above, intimately mixing the feed mixture comprising TAP with the oxidant may comprise running the feed mixture through one or more HSDs 40. Intimately mixing the feed mixture with oxidant at 310 may comprise running the feed mixture through two or more HSDs 40, in series or in parallel. Intimately mixing the feed mixture with oxidant may comprise running the feed mixture through three or more HSDs 40, in series and/or in parallel. Additional oxidant may be introduced into each subsequent HSD.

Separating Oxidation Product from Vapor 320. High shear terephthalic acid production method 300 further comprises separating oxidation product from vapor at 320. Following intimate mixing 310 and oxidation within HSD 40, high shear product comprising terephthalic acid is introduced into vessel 10. Vessel 10 is operated such that vapor/gas comprising vaporized medium (e.g., vaporized acetic acid medium) and gas such as, but not limited to, unreacted oxidant, carbon dioxide, methane, and other inert gases, are removed via vessel outlet line 16. During oxidation within HSD 40, heat of reaction produced by oxidation of the dialkyl benzene compound(s) may result in vaporization of a portion of the liquid medium. The vaporized liquid reaction medium along with oxygen-depleted process gas (i.e. oxidant) comprising unreacted oxygen, inerts which may have been introduced with the oxidant, minor amounts of decomposition products, and/or bromine-containing compounds are removed via vessel outlet line 16. Components (e.g. medium such as acetic acid) may be condensed from the removed vapor and returned to vessel 10 or HSD 40 as desired. Oxidation product comprising terephthalic acid is removed from vessel 10 by vessel 10 oxidation product outlet line 17. The oxidation product removed via line 17 generally comprises solid and dissolved TA, incomplete oxidation products (which may be less than that found in conventionally-obtained oxidation products), and medium (e.g., aqueous acetic acid). In embodiments, oxidation product removed from vessel 10 via line 17 further comprises oxidation catalyst, as discussed hereinabove.

Multiple Pass Operation. In the embodiment shown in FIG. 1, the system is configured for single pass operation. However, the output of HSD 40 may be run through a subsequent HSD. In some embodiments, it may be desirable to pass the contents of flow line 19, flow line 17 or a fraction thereof, through HSD 40 during a second pass. In this case, at least a portion of the contents of flow line 19 or 17 may be recycled, optionally pumped by pump 5 into line 13 and thence back into HSD 40. Additional reactants (e.g., oxidant) may be injected via line 22 into line 13, or may be added directly into the HSD. Due to the rapidity of the oxidation within HSD 40, multiple pass operation may not be necessary or desirable.

Multiple HSDs. In embodiments, oxidation product in HSD outlet line 19 or vessel 10 oxidation product outlet line 17 is fed into a second HSD, e.g. prior to downstream purification, utilization, or sale. In some embodiments, two or more HSDs like HSD 40, or configured differently, are aligned in series, and are used to promote further oxidation. In embodiments, the reactants pass through multiple HSDs 40 in serial or parallel flow. In embodiments, a second HSD is positioned upstream or downstream of vessel 10, whereby the oxidation product exiting HSD 40 or exiting vessel 10 via vessel 10 product outlet line 17 is introduced into a subsequent HSD for further oxidation. When multiple HSDs 40 are operated in series, additional oxidant may be injected into the inlet feed-stream of each HSD. For example, additional oxidant may be introduced into a second or subsequent HSD 40. In some embodiments, multiple HSDs 40 are operated in parallel, and the outlet products therefrom are introduced into one or more flow lines 19.

As discussed hereinabove, PTA used in the manufacture of polyester resins must meet certain minimum purity requirements. The purified condition of terephthalic acid refers mainly to the absence of significant concentrations of 4-carboxybenzaldehyde (4-CBA) and p-toluic acid that are present in significant quantities in crude commercially-available grades of terephthalic acid. Both CBA and toluic acid are partial oxidation products formed in the manufacture of PTA by the catalytic oxidation of p-xylene. The purified form also refers to the absence of color bodies that impart a characteristic yellow hue to the crude material. The color bodies are aromatic compounds having the structures of benzils, fluorenones, and/or anthraquinones, for example. 4-CBA and p-toluic acid are particularly detrimental to the polymerization process as they act as chain terminators during the condensation reaction between terephthalic acid and ethylene glycol in the production of poly(ethylene terephthalate) (PET), resulting in undesirably low molecular weight polyesters.

In embodiments, the oxidation product exiting HSD 40 via line 19 and/or the oxidation product extracted from vessel 10 via vessel 10 outlet line 17 obtained via high shear oxidation of a dialkylbenzene compound, e.g. p-xylene, contains acceptably low amounts of 4-CBA and/or p-toluic acid and/or color compounds, and further purification is not necessary prior to use. In embodiments, the total concentration of 4-CBA and p-toluic acid in the oxidation product is in the range of about 150 to 1100 ppmw based on the weight of the solids present. In embodiments, the total concentration of 4-CBA and p-toluic acid in the oxidation product is less than or about 150, 200, 300, 400, 500, 600, 700, 800, 900, 1000 or less than or about 1100 ppmw based on the weight of the solids present. In embodiments, the oxidation product within line 17 or 19 comprises from about 20-200 ppmw range or less of the color (i.e. yellow) compounds. As mentioned above, these compounds are colored aromatic compounds having the structures of benzil, fluorenone, and/or anthraquinone, which result from coupling side reactions occurring during the oxidation of p-xylene.

Separating TA from and/or Further Purifying Oxidation Product 330. High shear dicarboxylic acid production method 300 may further comprise separating terephthalic acid from the oxidation product and/or further purifying the (crude) oxidation product at 330. In embodiments, step 330 comprises separating the terephthalic acid from the oxidation product in line 17. Separating may comprise, for example, introducing the crude oxidation product from vessel 10 into separation apparatus 50. In embodiments, separation apparatus 50 is operable to separate terephthalic acid from the (e.g. aqueous acetic acid) medium to obtain product TA. For example, separation apparatus 50 may comprise a condenser system such as a water column and/or one or more flash evaporators. The separated TA may contain levels of impurities acceptable for desired end use, for example, the separated TA may be a PTA comprising less than about 150 ppmw p-toluic acid, or, alternatively, the separated TA may be a crude TA comprising contaminants (e.g. 4-CBA and/or p-toluic acid) that are removed by further purification steps.

Figure 5:
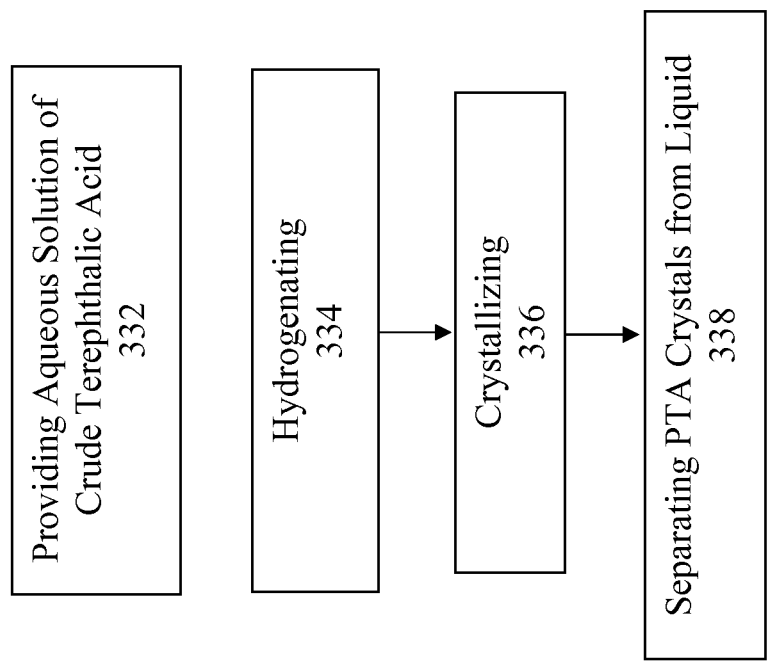
FIG. 5 is a box flow diagram of a method of purifying high shear oxidation product comprising terephthalic acid to provide PTA according to an embodiment of this disclosure.

TA product is removed from vessel 10 via line 17 as a slurry comprising aqueous medium (e.g., aqueous acetic acid) and may also contain catalyst (e.g., dissolved catalyst). The slurry removed from vessel 10 via oxidation product outlet line 17 may comprise from about 20 to about 40 weight percent solids. The oxidation product slurry comprises less than 1000, 900, 800, 700, 600, 500, 400, 300, 200, or 100 ppmw, based on the weight of solids, of incomplete oxidation products, mainly 4-carboxybenzaldehyde and p-toluic acid). FIG. 5 is a schematic of a method 330A used to separate TA from and/or further purify the oxidation product according to an embodiment of this disclosure. In embodiments, method 330A comprises providing an aqueous solution of crude terephthalic acid at 332. Providing an aqueous solution of crude TA 332 may comprise introducing the oxidation product from vessel 10 into a separation apparatus 50 operable to separate terephthalic acid from the carboxylic acid medium and replace the medium with water. The oxidation product slurry in line 17 may be cooled prior to introduction into separation apparatus 50.

Separation apparatus described in U.S. Patent App. No. 2002/0193630, which is hereby incorporated herein in its entirety for all purposes not contrary to this disclosure, may be utilized. As discussed hereinabove, separation apparatus 50 may comprise one or more centrifuges, filtration units, and/or evaporators (e.g. flash evaporators) operable to separate crude TA from the oxidation product in line 19 or 17 and one or more mixing units operable to form an aqueous slurry of the separated TA. The one or more mixing units may be operable to heat the contents therein and dissolve the separated TA (and possibly impurities) in water, providing an aqueous solution. The aqueous solution comprising dicarboxylic acid may comprise from about 10 to about 35 weight percent dicarboxylic acid solids in water or from about 25 to about 35 weight percent dicarboxylic acid in water. The dicarboxylic acid solution may be formed by heating the solvent or slurry of dicarboxylic acid to a temperature that is sufficient to dissolve the dicarboxylic acid at the concentration desired, e.g., temperatures in the range of about 260° C. to 320° C. Solution temperatures in the range of about 260° C. to 320° C. using a solvent such as water require that the solution be maintained at an elevated pressure, e.g., a pressure in the range of about 46.9 to 113 bars absolute (680-1640 pounds per square inch absolute (psia). In embodiments, water 50 is introduced into apparatus 50, for example, via line 52 and (e.g. monocarboxylic acid) medium removed via reaction medium outlet line 54. An aqueous solution of crude TA may be removed from separation apparatus 50 via separated product outlet line 56. The aqueous solution may be removed from separation apparatus 50 at elevated temperature and pressure, as known in the art.

Method 330A may further comprise hydrogenating the aqueous solution of TA at 334. The impurities within the crude TA may be hydrogenated by introducing the aqueous solution of crude terephthalic acid into hydrogenation apparatus 60, for example, via line 56. Within hydrogenation apparatus 60, the aqueous TA solution is subjected to reducing conditions, whereby 4-carboxybenzaldehyde is converted to p-toluic acid and the color bodies or color body precursors are converted to colorless compounds. For example, fluorenones and 4-CBA are converted (hydrogenated) to fluorenes and p-toluic acid, respectively. Unreacted hydrogen may be removed, for example, via line 63. In embodiments, unreacted hydrogen is recycled to hydrogenation apparatus 60 via line 62.

Hydrogen is introduced into hydrogenation apparatus 60 via gas inlet line 62 and contacts the aqueous dicarboxylic acid solution introduced into hydrogenation apparatus 60 via line 56. Hydrogenation apparatus 60 contains a hydrogenation catalyst, which may comprise, for example, a noble Group VIII metal on a catalyst support material (e.g. palladium on a carbon support), as known in the art. The liquid phase hydrogenation may be performed at elevated temperature, for example, in the case of TA the hydrogenation temperature may be a temperature in the range of from about 200° C. to about 375° C.

Assuming that there is substantially complete conversion of 4-CBA to p-toluic acid and assuming that the aqueous terephthalic acid solution fed to the hydrogenation apparatus 60 has a combined total concentration of 4-CBA and p-toluic acid of less than about X ppmw, e.g., about 400 to 900 ppmw, then the concentration of p-toluic acid alone in the product stream from hydrogenation apparatus 60 is less than about X ppmw, based on the terephthalic acid present.

In embodiments, hydrogenation apparatus 60 comprises a HSD. In such an embodiment, hydrogen and aqueous dicarboxylic acid solution are introduced into the HSD such that conversion of 4-CBA to p-toluic acid occurs. Hydrogenation catalyst may be introduced into the HSD along with the aqueous solution, or, in instances, may be fixed on a contact surface (e.g., a rotor and/or a stator) within the HSD, as discussed hereinabove with regard to oxidation catalyst.

Following hydrogenation, various separation and isolation techniques may be utilized to obtain purified terephthalic acid. As known in the art, such techniques include, but are not limited to, a wide variety of solid-liquid separation methods including crystallization, centrifugation, filtration, and combinations thereof. In embodiments, method 330A further comprises crystallizing purified TA from the hydrogenation product at 336. In such embodiments, further separation/isolation may comprise introducing hydrogenation product into crystallization apparatus 70 via hydrogenation product outlet line 64. Before the precipitation process, e.g. crystallization, and while substantially all of the terephthalic acid and other components are still in solution, the reaction medium may be treated so as to remove certain components. For example, the reaction medium may be treated to remove catalyst metal ions by ion exchange techniques using for instance a cationic exchange resin or by electrodialysis techniques involving ion exchange membranes, as known in the art and described, for example, in U.S. Pat. No. 6,307,099, which is hereby incorporated herein in its entirety for all purposes not contrary to this disclosure.

The temperature of the hydrogenation product in line 64 may be in the range of from about 260° C. to about 320° C. The hydrogenation product is fed to a crystallization apparatus 70. Crystallization apparatus 70 may comprise a plurality or sequence of series-connected crystallizer stages that together operate to reduce the temperature of the hydrogenation product in line 64 to a lower temperature, for example about 75° C. to about 180° C., from about 90° C. to about 150° C., or from about 90° C. to about 110° C. The reduction in temperature is accompanied by a concurrent precipitation of terephthalic acid from solution in the form of a white crystalline solid. The crystallization zone may comprise two to eight, three to six, or four to five crystallizers or crystallizer stages. The numbers of crystallizer stages employed in the process may affect the quality of the final product. Staging of the temperatures of the sequence of series-connected crystallizer stages may be adjusted to increase the purity of the final product with respect to p-toluic acid. Crystallization apparatus 70 may be operated as described in U.S. Patent App. 2002/0193630.

Crystallization apparatus 70 may comprise a staged equilibrium system wherein evaporation is controlled against back pressure regulation in multiple crystallizer stages to control the rate at which the hydrogenation product is crystallized. For terephthalic acid, shock cooling of the hydrogenation product to temperatures below 165° C. may be undesirable, as it promotes the co-precipitation (co-crystallization) of impurities, particularly p-toluic acid which is an undesirable contaminant of PTA.

U.S. Pat. No. 3,931,305 discloses that the primary factor determining the impurity concentration in the terephthalic acid product is the lowest temperature to which the post-hydrogenation stream is flashed. The impurity concentration is less a function of the rate at which the hydrogenation product is cooled. Thusly, in embodiments, a majority of the terephthalic acid is crystallized within crystallization apparatus 70 at a temperature greater than about 160° C. to about 185° C. Above 185° C., substantial undesirable p-toluic acid co-crystallization occurs. Evaporated solvent may be removed from crystallization apparatus 70 via one or more outlet lines 72.

Method 330A may further comprise separating purified TA (or PTA) crystals produced via crystallization at step 336 from the liquid solvent at step 338. The crystallization product removed from crystallization apparatus 70 via outlet line 74 may be introduced into one or more solid/liquid separators 80 configured to separate the crystalline terephthalic acid from the solvent. Solid/liquid separator 80 is any apparatus known to those of skill in the art to be suitable for the separation of crystallized TA from aqueous liquid. Solid/liquid separator 80 may comprise, for example, one or more filtration units (e.g. a rotary vacuum filter), centrifuges or settlers. Aqueous liquid removed from solid/liquid separator 80 may be removed via outlet line 82 and treated and/or recycled as desired. For example, some of the water extracted from solid/liquid separator 80 via outlet line 82 may be recycled to separation apparatus 50 via line 52 to create further aqueous solution of TA. Solid TA separated from liquids in separator 80 may be removed via purified dicarboxylic product outlet line 84. The TA product removed via line 84 may comprise PTA and contain less than 150 ppmw p-toluic acid. When the hydrogenation product in line 64 has a concentration from 500 to 6,000 ppmw p-toluic acid, post-crystallization filtration in separator 80 may be performed at a temperature in the range of from about 120° C. and about 150° C. to obtain a p-toluic acid concentration of 150 ppmw or less in the PTA product extracted via outlet line 84. Other suitable isolation techniques utilize efficient filtration, washing, and drying methods within the temperature range of 100° C. to 205° C. to mitigate precipitation of p-toluic acid.

Features. In embodiments, the oxidation product exiting HSD 40, vessel 10, and/or separation apparatus 50 comprises less than 1000, 900, 800, 700, 600, 500, 400, 300, 200, 100 or 50 ppmw of impurities including p-toluic acid and 4-CBA. In embodiments, the level of impurities in the purified TA exiting hydrogenation apparatus 60, crystallization apparatus 70, or solid/liquid separator 80 is less than about 1000, 900, 800, 700, 600, 500, 400, 300, 200, 100 or 50 ppmw. The system and method may be operable to provide greater than 5, 10, or 20 tons/h of desired dicarboxylic acid.

In embodiments, utilization of the disclosed system and method provides at least about a 30, 40, 50, 60, 70, or 80% reduction in the amount of impurities (e.g., a total of 4-CBA and p-toluic acid) in the oxidation product (relative to conventional oxidation) which must be removed to provide a suitable PTA. Concomitantly, utilization of the disclosed system and method may provide a significant cost savings because less downstream purification equipment and/or reduced-size equipment may be suitable to provide PTA.

The reduction in the concentration of impurities in the oxidation product facilitated by HSD 40 may allow for more efficient hydrogenation, or even the need for no further downstream purification in some applications. In embodiments, the hydrogenation apparatus 60 is reduced in size and/or the residence time of the aqueous solution within hydrogenation apparatus 60 may be reduced compared with conventional methods and systems.

Additionally, since the total concentration of 4-CBA and p-toluic acid fed to hydrogenation reactor 60 is reduced by the use of HSD 40, there is less p-toluic acid in the hydrogenation product exiting hydrogenation apparatus 60 via line 64 relative to the hydrogenation product from conventional purification processes. The number and/or the size of crystallization zones or crystallizers within crystallization apparatus 70 may thus be reduced, simplifying crystallization.

The amount of material, such as aqueous medium comprising dissolved impurities (e.g., extracted from system 100A via outlet line 82) that must be purged from the high shear system is reduced since the concentration of p-toluic acid is reduced.

Without wishing to be limited to a particular theory, it is believed that the level or degree of high shear mixing may be sufficient to increase rates of mass transfer and also produce localized non-ideal conditions (in terms of thermodynamics) that enable reactions to occur that would not otherwise be expected to occur based on Gibbs free energy predictions and/or increase the rate or extent of expected reactions. Localized non ideal conditions are believed to occur within the HSD resulting in increased temperatures and pressures with the most significant increase believed to be in localized pressures. The increases in pressure and temperature within the HSD are instantaneous and localized and quickly revert back to bulk or average system conditions once exiting the HSD. Without wishing to be limited by theory, in some cases, the HSD may induce cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006). The HSD of certain embodiments of the present system and methods may induce cavitation whereby one or more reactant is dissociated into free radicals, which then react. In embodiments, the extreme pressure at the tips of the rotors/stators leads to liquid phase reaction, and no cavitation is involved.

Various dimensions, sizes, quantities, volumes, rates, and other numerical parameters and numbers have been used for purposes of illustration and exemplification of the principles of the invention, and are not intended to limit the invention to the numerical parameters and numbers illustrated, described or otherwise stated herein. Likewise, unless specifically stated, the order of steps is not considered critical. The different teachings of the embodiments discussed below may be employed separately or in any suitable combination to produce desired results.

Production of Benzoic Acid

Systems and methods for accelerating production of benzoic acid, methylbenzoic acid isomers, and phthalic acids are disclosed. In accordance with certain embodiments, a method for producing benzoic acid or a methylbenzoic acid isomer is provided which comprises forming a dispersion comprising oxygen-containing gas bubbles dispersed in either toluene or a xylene isomer, wherein the bubbles have a mean diameter less than 1 micron; and subjecting the dispersion to reaction conditions comprising a pressure of less than about 1013 kPa and a temperature of less than about 160° C., whereby at least a portion of the toluene or xylene isomer is oxidized to form benzoic acid or a corresponding methylbenzoic acid isomer, respectively. In certain embodiments, the method comprises subjecting the oxygen-containing gas and the toluene or the xylene isomer to high shear mixing at a tip speed of at least 22.9 msec (4,500 ft/min). The high shear mixing potentially provides enhanced time, temperature and pressure conditions resulting in accelerated chemical reactions between multiphase reactants. Certain embodiments provide for the production of one or more methylbenzoic acid isomer (i.e., 2-, 3-, and/or 4-methylbenzoic acid) by partially oxidizing o-, m-, or p-xylene, respectively. In some embodiments, the methylbenzoic acid isomer is an intermediate compound, and the method further includes subjecting any unreacted xylene isomer and the intermediate compound to further oxidization, to form one or more phthalic acid isomer (i.e., 1,2-benzenedicarboxylic acid, 1,3-benzenedicarboxylic acid, and/or 1,4-benzenedicarboxylic acid).

In accordance with certain embodiments of the invention, a method is provided producing benzoic acid, which comprises forming a dispersion comprising oxygen-containing gas bubbles dispersed in toluene liquid phase, wherein the bubbles have a mean diameter less than 1 micron; and subjecting the dispersion to reaction conditions comprising pressure of less than about 1013 kPa and temperature of less than about 160° C., whereby at least a portion of the toluene is partially oxidized to form benzoic acid. In some embodiments, the gas bubbles have a mean diameter of less than 400 nm, and in some embodiments they are no more than 100 nm.

In accordance with certain embodiments of the invention, a method is provided for producing a methylbenzoic acid, which comprises forming a dispersion comprising oxygen-containing gas bubbles dispersed in a liquid phase comprising xylene, wherein the bubbles have a mean diameter less than 1 micron; and subjecting the dispersion to reaction conditions comprising pressure of less than about 1013 kPa and temperature of less than about 160° C., whereby at least a portion of the xylene is partially oxidized to form methylbenzoic acid, respectively, or a mixture thereof. In some embodiments, the gas bubbles have a mean diameter of less than 400 nm, and in some embodiments they are no more than 100 nm.

In accordance with certain embodiments of the invention, a system is provided which comprises at least one high shear mixing device configured for producing a dispersion of oxygen-containing gas bubbles in either toluene or a xylene isomer, wherein the dispersion has a mean bubble diameter of less than 400 nm. In some embodiments, the system further comprises a pump configured for delivering a liquid stream comprising the toluene or xylene isomer to the high shear mixing device. In some embodiments, the system further comprises a vessel configured for receiving the dispersion from the high shear mixer. Some embodiments of the system potentially make possible the production of benzoic acid or methylbenzoic acid isomers without the need for large volume reactors or the need for recovery of a substantial amount of unconverted toluene or xylene.

Certain embodiments of the methods potentially provide for more optimal time, temperature and pressure conditions than are otherwise possible, and which potentially increase the rate of the gas/liquid phase process. Certain embodiments of the above-described methods or systems potentially provide overall cost reduction by operating at lower temperature and/or pressure, providing increased product per unit of catalyst consumed, decreased reaction time, and/or reduced capital and/or operating costs.

The present methods and systems for the production of benzoic acid and 2-, 3-, or 4-methyl benzoic acid via liquid phase partial oxidation of toluene and o-, m-, or p-xylene, respectively, employ an external high shear mechanical device to provide rapid contact and mixing of chemical ingredients in a controlled environment in the reactor/mixer device. Some embodiments of the methods and systems are also suitable for production of the further oxidation products of o-, m-, or p-xylene, or of 2-, 3- or 4-methylbenzoic acid, i.e., 1,2-benzenedicarboxylic acid, 1,3-benzenedicarboxylic acid, and 1,4-benzenedicarboxylic acid, respectively. The high shear device reduces the mass transfer limitations on the reaction and thus increases the overall reaction rate. For the purposes of this disclosure, "xylene" includes the ortho, meta, and para isomers of xylene. The term "methylbenzoic acid" includes the 2-, 3-, and 4-methylbenzoic acid isomers.

Chemical reactions involving liquids, gases and solids rely on the laws of kinetics that involve time, temperature, and pressure to define the rate of reactions. In cases where it is desirable to react two or more raw materials of different phases (e.g. solid and liquid; liquid and gas; solid, liquid and gas), one of the limiting factors in controlling the rate of reaction involves the contact time of the reactants. In the case of heterogeneously catalyzed reactions there is the additional rate limiting factor of having the reacted products removed from the surface of the catalyst to enable the catalyst to catalyze further reactants. Contact time for the reactants and/or catalyst is often controlled by mixing which provides contact with two or more reactants involved in a chemical reaction. A reactor assembly that comprises an external high shear device or mixer as described herein makes possible decreased mass transfer limitations and thereby allows the reaction to more closely approach kinetic limitations. When reaction rates are accelerated, residence times may be decreased, thereby increasing obtainable throughput. Product yield may be increased as a result of the high shear system and process. Alternatively, if the product yield of an existing process is acceptable, decreasing the required residence time by incorporation of suitable high shear may allow for the use of lower temperatures and/or pressures than conventional processes.

Figure 6:
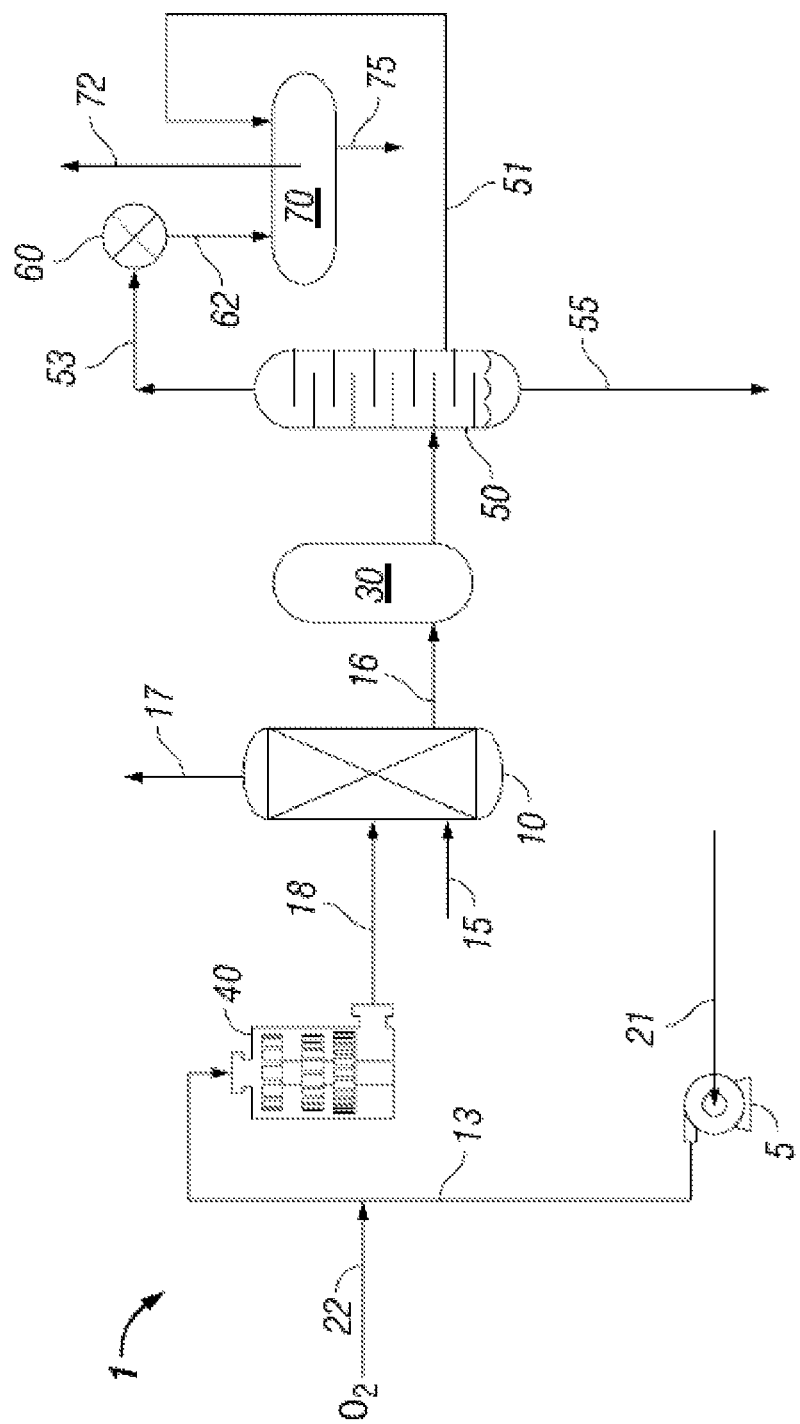
FIG. 6 is a process flow diagram of a process for production of either benzoic acid or methyl benzoic acid, according to certain embodiments of this disclosure.

System for Production of Benzoic Acid or Methylbenzoic Acid. A high shear benzoic acid or methylbenzoic acid production system will now be described in relation to FIG. 6, which is a process flow diagram of an embodiment of a high shear system 1 for the production of benzoic acid via partial oxidation of toluene, or for the production of methylbenzoic acid by partial oxidation of xylene. The basic components of a representative system include external high shear mixing device (HSD) 40, vessel 10, and pump 5. As shown in FIG. 6, the high shear device is located external to vessel/reactor 10. Each of these components is further described in more detail below. Line 21 is connected to pump 5 for introducing either toluene or xylene reactant. Line 13 connects pump 5 to HSD 40, and line 18 connects HSD 40 to vessel 10. Line 22 is connected to line 13 for introducing an oxygen-containing gas (e.g., $O_2$ or air). Line 17 is connected to vessel 10 for removal of unreacted toluene or xylene vapor, unreacted oxygen, nitrogen, and other reaction gases. Additional components or process steps may be incorporated between vessel 10 and HSD 40, or ahead of pump 5 or HSD 40, if desired. For example, line 72 may be connected to line 21 or line 13, to provide for multi-pass operation, if desired.

In some embodiments, HSD 40 comprises a catalytic surface made of a suitable oxidation catalyst that promotes the oxidation reactions to form benzoic acid or methylbenzoic acid. In some cases, vessel 10 is omitted. In some other cases, vessel 10 is used in conjunction with HSD comprising such catalytic surface.

High Shear Mixing Device. External high shear mixing device (HSD) 40, also sometimes referred to as a high shear mixer, is configured for receiving an inlet stream via line 13, comprising toluene or xylene and molecular oxygen. Alternatively, HSD 40 may be configured for receiving the liquid and gaseous reactant streams via separate inlet lines (not shown). Although only one high shear device is shown in FIG. 6, it should be understood that some embodiments of the system may have two or more high shear mixing devices arranged either in series or parallel flow. HSD 40 is a mechanical device that utilizes one or more generators comprising a rotor/stator combination, each of which having a fixed gap between the stator and rotor. HSD 40 is configured in such a way that it is capable of producing submicron (i.e., less than 1 micron in diameter) and micron-sized bubbles in a reactant mixture flowing through the mixer. The high shear mixer comprises an enclosure or housing so that the pressure and temperature of the reaction mixture may be controlled.

High shear mixing devices are generally divided into three general classes, based upon their ability to mix fluids. Mixing is the process of reducing the size of particles or inhomogeneous species within the fluid. One metric for the degree or thoroughness of mixing is the energy density per unit volume that the mixing device generates to disrupt the fluid particles. The classes are distinguished based on delivered energy densities. Three classes of industrial mixers having sufficient energy density to consistently produce mixtures or emulsions with particle sizes in the range of submicron to 50 microns include homogenization valve systems, colloid mills and high speed mixers. In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average particle sizes in the 0-1 micron range.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between the low energy devices and homogenization valve systems, in terms of the mixing energy density delivered to the fluid, are colloid mills, which are classified as intermediate energy devices. A typical colloid mill configuration includes a conical or disk rotor that is separated from a complementary, liquid-cooled stator by a closely-controlled rotor-stator gap, which is commonly between 0.0254-10.16 mm (0.001-0.40 inch). Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1-25 microns in the processed fluid. These capabilities render colloid mills appropriate for a variety of applications including colloid and oil/water-based emulsion processing such as that required for cosmetics, mayonnaise, or silicone/silver amalgam formation, to roofing-tar mixing.

An approximation of energy input into the fluid (kW/L/min) can be estimated by measuring the motor energy (kW) and fluid output (L/min). Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance transcribed by the rotor tip, $2\pi R$, where R is the radius of the rotor (in meters, for example) times the frequency of revolution (in revolutions per minute). A colloid mill, for example, may have a tip speed in excess of 22.9 msec (4500 ft/min) and may exceed 40 msec (7900 ft/min). For the purposes of this disclosure, the term "high shear" refers to mechanical rotor stator devices (e.g., colloid mills or rotor/stator mixers) that are capable of tip speeds in excess of 5.1 msec (1000 ft/min) and require an external mechanically driven power device to drive energy into the stream of materials to be reacted. For example, in HSD 40, a tip speed in excess of 22.9 msec (4500 ft/min) is achievable, and may exceed 40 msec (7900 ft/min). In some embodiments, HSD 40 is capable of delivering at least 300 L/h with a power consumption of about 1.5 kW at a nominal tip speed of at least 22.9 msec (4500 ft/min).

HSD 40 combines high tip speeds with a very small shear gap to produce significant shear on the material being processed. The amount of shear will be dependent on the viscosity of the fluid. Accordingly, a local region of elevated pressure and temperature is created at the tip of the rotor during operation of the high shear device. In some cases the locally elevated pressure is about 1034.2 MPa (150,000 psi). In some cases the locally elevated temperature is about 500° C. In some cases these local pressure and temperature elevations may persist for nano or pico seconds.

HSD 40 is capable of highly dispersing or transporting oxygen into a main liquid phase comprising toluene or xylene, in some cases together with a soluble catalyst or catalyst slurry, with which it would normally be immiscible, at conditions such that at least a portion of the oxygen reacts with the toluene or xylene to produce a product stream comprising benzoic acid or methylbenzoic acid, respectively. In some embodiments, HSD 40 comprises a colloid mill. Suitable colloidal mills are manufactured by IKA® Works, Inc. Wilmington, NC and APV North America, Inc. Wilmington, MA, for example. In some instances, HSD 40 comprises the DISPAX® Reactor of IKA® Works, Inc. Several models are available having various inlet/outlet connections, horsepower, nominal tip speeds, output rpm, and nominal flow rate. Selection of a particular device will depend on specific throughput requirements for the intended application, and on the desired bubble size in the outlet dispersion from the high shear mixer. In some embodiments, selection of the appropriate mixing tools (generators) within HSD 40 may allow for catalyst size reduction/increase in catalyst surface area.

The high shear device comprises at least one revolving element that creates the mechanical force applied to the reactants. The high shear device comprises at least one stator and at least one rotor separated by a clearance. For example, the rotors may be conical or disk shaped and may be separated from a complementary-shaped stator; both the rotor and stator may comprise a plurality of circumferentially-spaced teeth. In some embodiments, the stator(s) are adjustable to obtain the desired gap between the rotor and the stator of each generator (rotor/stator set). Grooves in the rotor and/or stator may change directions in alternate stages for increased turbulence. Each generator may be driven by any suitable drive system configured for providing the necessary rotation.

In some embodiments, the minimum clearance between the stator and the rotor is in the range of from about 0.0254 mm to about 3.175 mm (about 0.001 inch to about 0.125 inch). In certain embodiments, the minimum clearance between the stator and rotor is about 1.524 mm (0.060 inch). In certain configurations, the minimum clearance between the rotor and stator is at least 1.778 mm (0.07 inch). The shear rate produced by the high shear mixer may vary with longitudinal position along the flow pathway. In some embodiments, the rotor is set to rotate at a speed commensurate with the diameter of the rotor and the desired tip speed. In some embodiments, the colloidal mill has a fixed clearance between the stator and rotor. Alternatively, the colloid mill has adjustable clearance.

In some embodiments, HSD 40 comprises a single stage dispersing chamber (i.e., a single rotor/stator combination, a single generator). In some embodiments, high shear device 40 is a multiple stage inline disperser and comprises a plurality of generators. In certain embodiments, HSD 40 comprises at least two generators. In other embodiments, high shear device 40 comprises at least 3 high shear generators. In some embodiments, high shear device 40 is a multistage mixer whereby the shear rate (which varies proportionately with tip speed and inversely with rotor/stator gap) varies with longitudinal position along the flow pathway, as further described herein below.

In some embodiments, each stage of the external high shear device has interchangeable mixing tools, offering flexibility. For example, the DR 2000/4 DISPAX® Reactor of IKA® Works, Inc. Wilmington, NC and APV North America, Inc. Wilmington, MA, comprises a three stage dispersing module. This module may comprise up to three rotor/stator combinations (generators), with choice of fine, medium, coarse, and super-fine for each stage. This allows for creation of dispersions having a narrow distribution of the desired bubble size. In some embodiments, each of the stages is operated with super-fine generator. In some embodiments, at least one of the generator sets has a rotor/stator minimum clearance of greater than about 5.08 mm (0.20 inch). In some embodiments, at least one of the generator sets has a minimum rotor/stator clearance of greater than about 1.778 mm (0.07 inch). In some embodiments the rotors are 60 mm and the stators are 64 mm in diameter, providing a clearance of about 4 mm.

Vessel. Vessel or reactor 10 is any type of vessel in which a multiphase reaction can be propagated to carry out the above-described conversion reaction(s). For instance, a continuous or semi-continuous stirred tank reactor, or one or more batch reactors may be employed in series or in parallel. In some applications vessel 10 may be a tower reactor, and in others a tubular reactor or multi-tubular reactor. A catalyst inlet line 15 may be connected to vessel 10 for receiving a catalyst solution or slurry during operation of the system.

Vessel 10 may include one or more of the following components: stirring system, heating and/or cooling capabilities, pressure measurement instrumentation, temperature measurement instrumentation, one or more injection points, and level regulator (not shown), as are known in the art of reaction vessel design. For example, a stirring system may include a motor driven mixer. A heating and/or cooling apparatus may comprise, for example, a heat exchanger. Alternatively, as much of the conversion reaction may occur within HSD 40 in some embodiments, vessel 10 may serve primarily as a storage vessel in some cases. Although generally less desired, in some applications vessel 10 may be omitted, particularly if multiple high shear mixers/reactors are employed in series, as further described below.

Heat Transfer Devices. In addition to the above-mentioned heating/cooling capabilities of vessel 10, other external or internal heat transfer devices for heating or cooling a process stream are also contemplated in variations of the embodiments illustrated in FIG. 6. Some suitable locations for one or more such heat transfer devices are between pump 5 and HSD 40, between HSD 40 and vessel 10, and between vessel 10 and pump 5 when system 1 is operated in multi-pass mode. Some non-limiting examples of such heat transfer devices are shell, tube, plate, and coil heat exchangers, as are known in the art.

Pumps. Pump 5 is configured for either continuous or semi-continuous operation, and may be any suitable pumping device that is capable of providing greater than 203 kPa (2 atm) pressure, preferably greater than 304 kPa (3 atm) pressure, to allow controlled flow through HSD 40 and system 1. For example, a Roper Type 1 gear pump, Roper Pump Company (Commerce Georgia) Dayton Pressure Booster Pump Model 2P372E, Dayton Electric Co (Niles, Ill.) is one suitable pump. Preferably, all contact parts of the pump comprise stainless steel. In some embodiments of the system, pump 5 is capable of pressures greater than about 2027 kPa (20 atm). In addition to pump 5, one or more additional, high pressure pump (not shown) may be included in the system illustrated in FIG. 6. For example, a booster pump, which may be similar to pump 5, may be included between HSD 40 and vessel 10 for boosting the pressure into vessel 10. As another example, a supplemental feed pump, which may be similar to pump 5, may be included for introducing additional reactants or catalyst into vessel 10. As still another example, a compressor type pump may be positioned between line 17 and HSD 40 for recycling gas from vessel 10 to an inlet of the high shear unit.

In some embodiments, a high shear system 1 further includes a fractionating column 50 connected to vessel 10 via line 16, as illustrated in FIG. 6. A preheater 30 may be included in line 16. Bottom line 55, intermediate line 51 and head line 53 are connected to column 50 for removal of benzoic acid, small amounts of water and by-products, and unconverted toluene, respectively. Line 53 connects to a condenser 60, which in turn is connected to settling tank or settler 70 via line 62. Intermediates line 51 also connects to settling tank 70. Line 75 is connected to settler 70 for removal of an aqueous phase, and line 72 is connected to settler 70 for removal of a supernatant toluene or xylene phase. If desired, line 72 may be connected to line 21 for recycling the unreacted toluene or xylene and intermediates into HSD 40 via pump 5.

Production of Benzoic Acid or Methylbenzoic Acids. In operation for the catalytic production of benzoic acid from toluene, or, alternatively, for the independent production of 2-, 3-, or 4-methylbenzoic acid from o-, m-, or p-xylene, respectively, a dispersible oxygen-containing gas stream is introduced into system 1 via line 22, and combined in line 13 with either a toluene- or xylene-containing liquid stream, depending upon whether benzoic acid or a particular isomer of methylbenzoic acid, or mixture of such isomers, is the desired product. For ease of reference, the o-, m-, and p-xylene isomers are individually and collectively referred to as "xylene" herein, although it should be understood that a specific isomer or combination of isomers could be substituted in place of the generic xylene. Likewise, use of the generic term "methylbenzoic acid" is this disclosure represents each of the 2-, 3- and 4-methylbenzoic acid isomers, individually and collectively, where the context allows. The oxygen-containing gas may be air, oxygen, or any other suitable molecular oxygen-containing gas, or mixture of gases, for example. Alternatively, the oxygen-containing gas may be fed directly into HSD 40, instead of being combined with the liquid reactant (i.e., toluene or xylene) in line 13. Pump 5 is operated to pump the liquid reactant (toluene or xylene) through line 21, and to build pressure and feed HSD 40, providing a controlled flow throughout high shear mixer (HSD) 40 and high shear system 1. In some embodiments, pump 5 increases the pressure of the toluene or xylene stream to greater than 203 kPa (2 atm), preferably greater than about 304 kPa (3 atm). In some embodiments the pressure is about 1013 kPa (10 atm).

After pumping, the oxygen and liquid reactants are mixed within HSD 40, which serves to create a fine dispersion of the oxygen-containing gas in the toluene or xylene. In some embodiments it may create a fine mixture, emulsion or dispersion of the reactants, which may also include catalyst. As used herein, the term "dispersion" refers to a liquefied mixture that contains two distinguishable substances (or phases) that will not readily mix and dissolve together. A dispersion comprises a continuous phase (or matrix), which holds therein discontinuous droplets, bubbles, and/or particles of the other phase or substance. The term dispersion may thus refer to foams comprising gas bubbles suspended in a liquid continuous phase, emulsions in which droplets of a first liquid are dispersed throughout a continuous phase comprising a second liquid with which the first liquid is immiscible, and continuous liquid phases throughout which solid particles are distributed. The term "dispersion" encompasses continuous liquid phases throughout which gas bubbles are distributed, continuous liquid phases throughout which solid particles (e.g., solid catalyst) are distributed, continuous phases of a first liquid throughout which droplets of a second liquid that is substantially insoluble in the continuous phase are distributed, and liquid phases throughout which any one or a combination of solid particles, immiscible liquid droplets, and gas bubbles are distributed. Hence, a dispersion can exist as a homogeneous mixture in some cases (e.g., liquid/liquid phase), or as a heterogeneous mixture (e.g., gas/liquid, solid/liquid, or gas/solid/liquid), depending on the nature of the materials selected for combination.

In HSD 40, the oxygen-containing gas and toluene or xylene are highly dispersed such that nanobubbles, submicron-sized bubbles, and microbubbles of the gaseous reactants are formed for superior dissolution into solution and enhancement of reactant mixing. For example, disperser IKA® model DR 2000/4, a high shear, three stage dispersing device configured with three rotors in combination with stators, aligned in series, is used to create the dispersion of dispersible oxygen-containing gas in liquid medium comprising toluene or xylene (i.e., "the reactants"). The rotor/stator sets may be configured as illustrated in FIG. 3, for example. For some applications, the direction of rotation of the generators may be opposite that shown by arrow 265 (e.g., clockwise or counterclockwise about axis of rotation 260). The combined reactants enter the high shear mixer via line 13 and enter a first stage rotor/stator combination having circumferentially spaced first stage shear openings. In some applications, the direction of flow of the reactant stream entering inlet 205 corresponds to the axis of rotation 260. The coarse dispersion exiting the first stage enters the second rotor/stator stage, having second stage shear openings. The reduced bubble-size dispersion emerging from the second stage enters the third stage rotor/stator combination having third stage shear openings. The dispersion exits the high shear mixer via line 18. In some embodiments, the shear rate increases stepwise longitudinally along the direction of the flow. For example, in some embodiments, the shear rate in the first rotor/stator stage is greater than the shear rate in subsequent stage(s). In other embodiments, the shear rate is substantially constant along the direction of the flow, with the stage or stages being the same. If the high shear mixer includes a PTFE seal, for example, the seal may be cooled using any suitable technique that is known in the art. For example, the reactant stream flowing in line 13 may be used to cool the seal and in so doing be preheated as desired prior to entering the high shear mixer.

The rotor of HSD 40 is set to rotate at a speed commensurate with the diameter of the rotor and the desired tip speed. As described above, the high shear mixer (e.g., colloid mill) has either a fixed clearance between the stator and rotor or has adjustable clearance. HSD 40 serves to intimately mix the oxygen-containing gas and the reactant liquid (i.e., toluene or xylene). In some embodiments of the process, the transport resistance of the reactants is reduced by operation of the high shear mixer such that the velocity of the reaction is increased by greater than a factor of about 5. In some embodiments, the velocity of the reaction is increased by at least a factor of 10. In some embodiments, the velocity is increased by a factor in the range of about 10 to about 100 fold. In some embodiments, HSD 40 delivers at least 300 L/h with a power consumption of 1.5 kW at a nominal tip speed of at least 22.9 msec (4500 ft/min), and which may exceed 40 msec (7900 ft/min). In some embodiments, the mixture is subjected to a shear rate greater than $20{,}000\ s^{-1}$.

Although measurement of instantaneous temperature and pressure at the tip of a rotating shear unit or revolving element in HSD 40 is difficult, it is estimated that the localized temperature seen by the intimately mixed reactants is in excess of 500° C. and at pressures in excess of 500 kg/cm$^2$ under cavitation conditions. The high shear mixing results in dispersion of the oxygen-containing gas in micron or submicron-sized bubbles (i.e., mean diameter less than 1 micron). In some embodiments, the resultant dispersion has an average bubble size less than about 1.5 μm. Accordingly, the dispersion exiting HSD 40 via line 18 comprises micron and/or submicron-sized gas bubbles. In some embodiments, the mean bubble size is less than one micron. In some embodiments, the mean bubble size is in the range of about 0.4 μm to about 1.5 μm. In some embodiments, the mean bubble size is less than about 400 nm, is in the range of about 200 nm to about 400 nm, or is about 100 nm in some cases. In many embodiments, the microbubble dispersion is able to remain dispersed at atmospheric pressure for at least 15 minutes.

Once dispersed, the resulting gas/toluene dispersion or gas/xylene dispersion exits HSD 40 via line 18 and feeds into vessel 10, as illustrated in FIG. 6. As a result of the intimate mixing of the reactants prior to entering vessel 10, a significant portion of the chemical reaction may take place in HSD 40, with or without the presence of a catalyst. Accordingly, in some embodiments, reactor/vessel 10 may be used primarily for heating and separation of volatile reaction products from the benzoic acid or methylbenzoic acid product. Alternatively, or additionally, vessel 10 may serve as a primary reaction vessel where most of the benzoic acid or methylbenzoic acid product is produced. Vessel/reactor 10 may be operated in either continuous or semi-continuous flow mode, or it may be operated in batch mode. The contents of vessel 10 may be maintained at a specified reaction temperature using heating and/or cooling capabilities (e.g., cooling coils) and temperature measurement instrumentation. Pressure in the vessel may be monitored using suitable pressure measurement instrumentation, and the level of reactants in the vessel may be controlled using a level regulator (not shown), employing techniques that are known to those of skill in the art. The contents are stirred continuously or semi-continuously.

Catalyst. If a catalyst is used to promote the partial oxidation reaction, it may be introduced into the vessel via line 15, as an aqueous or nonaqueous slurry or stream. Alternatively, or additionally, catalyst may be added elsewhere in the system 1. For example, catalyst solution or slurry may be injected into line 21. In some embodiments, line 21 may contain a flowing toluene or xylene stream and/or toluene- or xylene-containing recycle stream from vessel 10, via line 72, which may be connected to line 21. A suitable soluble catalyst may be based on a metal salt or oxide, such as a cobalt salt, e.g., cobalt acetate, cobalt naphthenate, cobalt benzoate, cobalt oenanthate, and combinations thereof. In some embodiments, catalyst is present in vessel 10 at a concentration of from about 500 ppm to about 3000 ppm (parts per million), expressed in terms of parts of metal with respect to the toluene or xylene to be oxidized. In some embodiments, the catalyst is added continuously to vessel 10 via line 15. Without wishing to be limited by theory, it is believed that sub-micron particles or bubbles dispersed in a liquid undergo movement primarily through Brownian motion effects. The bubbles in the product dispersion created by HSD 40 may have greater mobility through boundary layers of undissolved catalyst particles, thereby facilitating and accelerating the catalytic reaction through enhanced transport of reactants.

The bulk or global operating temperature of the reactants is desirably maintained below their flash points. In some embodiments, the operating conditions of system 1 comprise a temperature in the range of from about 100° C. to about 230° C. In embodiments, the temperature is in the range of from about 160° C. to 180° C. In specific embodiments, the reaction temperature in vessel 10, in particular, is in the range of from about 155° C. to about 160° C. In some embodiments, the reaction pressure in vessel 10 is in the range of from about 203 kPa (2 atm) to about 5573 kPa-6080 kPa (55-60 atm). In some embodiments, reaction pressure is in the range of from about 811 kPa (8 atm) to about 1520 kPa (15 atm).

If desired, the dispersion may be further processed prior to entering vessel 10. In vessel 10, benzoic acid or methylbenzoic acid production occurs via catalytic partial oxidation. The contents of the vessel are stirred continuously or semi-continuously, the temperature of the reactants is controlled (e.g., using a heat exchanger), and the fluid level inside vessel 10 is regulated using standard techniques. Benzoic acid or methylbenzoic acid may be produced either continuously, semi-continuously or batch wise, as desired for a particular application. Any reaction gas that is produced exits reactor 10 via gas line 17. This gas stream may comprise unreacted toluene or xylene vapor, nitrogen and oxygen, for example. Preferably the reactants are selected so that the gas stream comprises less than about 6% oxygen by weight. In some embodiments, the reaction gas stream in line 17 comprises from about 1% to about 4% oxygen by weight. The reaction gas removed via line 17 may be further treated, and the components may be recycled, as desired. For example, all or a portion of the gases may be returned to HSD 40 by injection into line 13.

The reaction product stream comprising non-converted liquid toluene, benzoic acid, benzaldehyde, and other derivatives and byproducts exits vessel 10 by way of at least one line 16. Likewise, when xylene serves as the liquid reactant, the corresponding reaction product stream comprises non-converted xylene, methylbenzoic acid, and any derivatives and byproducts. The benzoic acid or methylbenzoic acid may be recovered and treated as known to those of skill in the art. For example, suitable further treatments are described in U.S. Pat. No. 4,578,511 and UK Patent No. 1,219,453. For example, the product stream flowing through line 16 may comprise from about 20% to about 35% benzoic acid or methylbenzoic acid (by weight), and is heated in preheater 30 and fed to a fractionating column 50, as illustrated in FIG. 6. Fractionating column 50 yields a benzoic or methylbenzoic acid fraction 55 which is removed and withdrawn from bottoms line 55. Column 50 also yields a heads fraction and an intermediates fraction, which contain unconverted toluene or xylene and small amounts of water and by-products, respectively. The heads fraction is removed via line 53, condensed in condenser 60, and sent to settling tank 70 via line 62. The intermediates fraction is also fed into settler 70 where it is combined with the condensate from condenser 60 and line 62. In settler 70, an aqueous phase settles out and is discharged via line 75. A supernatant toluene or xylene phase in settling tank 70 may be recycled into system 1 by returning the toluene or xylene phase, via line 72, to line 21, for example.

Multiple Pass Operation. In the embodiment shown in FIG. 6, the system is configured for single pass operation, wherein the output from vessel 10 goes directly to further processing for recovery of benzoic acid or methylbenzoic acid product. In some embodiments it may be desirable to pass the contents of vessel 10, or a liquid fraction containing unreacted toluene or xylene, through HSD 40 during a second pass. In this case, line 16 is connected to line 21, and the recycle stream from vessel 10 is pumped by pump 5 into line 13 and thence into HSD 40. Additional oxygen-containing gas may be injected via line 22 into line 13, or it may be added directly into the high shear mixer (not shown).

Multiple High Shear Mixing Devices. In some embodiments, two or more high shear devices like HSD 40, or configured differently, are aligned in series, and are used to further enhance the reaction. Their operation may be in either batch or continuous mode. In some instances in which a single pass or "once through" process is desired, the use of multiple high shear devices in series may also be advantageous. In some embodiments where multiple high shear devices are operated in series, vessel 10 may be omitted. When multiple high shear devices are operated in series, additional reactant(s) may be injected into the inlet feed stream of each device. In some embodiments, multiple high shear devices 40 are operated in parallel, and the outlet dispersions therefrom are introduced into one or more vessel 10.

Production of Phthalic Acids. If desired, the composition of the initial oxygen and xylene reactants used in the above-described methods may be modified so as to provide an increased amount of oxygen, or to provide increased exposure of the xylene to oxygen in the dispersion, compared to the partial oxidation reaction conditions. In this case, the o-, m-, or p-xylene may be converted directly to 1,2-benzenedicarboxylic acid (phthalic acid), 1,3-benzenedicarboxylic acid (isophthalic acid), or 1,4-benzenedicarboxylic acid (terephthalic acid or p-phthalic acid), depending on which xylene isomer is used as the feed stock. If the process is operated in recycle or multiple pass mode, any unreacted o-, m-, or p-xylene and partial oxidation product (i.e., 2-, 3- or 4-methylbenzoic acid) may be subjected to further oxidization, if desired, by supplying additional oxygen to the reactant stream entering HSD 40, or extended processing in HSD 40. This causes the second methyl group of the xylene isomer(s) to be oxidized to the carboxylate, to form the corresponding oxidation product(s) 1,2-benzenedicarboxylic acid, 1,3-benzenedicarboxylic acid, or 1,4-benzenedicarboxylic acid product.

The application of enhanced mixing of the reactants by HSD 40 potentially causes greater conversion of toluene to benzoic acid, or greater conversion of xylene to methylbenzoic acid, or to the corresponding phthalic acid, in various embodiments of the method. In some embodiments, the enhanced mixing potentiates an increase in throughput of the process stream. In some embodiments, the high shear mixing device is incorporated into an established process, thereby enabling an increase in production (i.e., greater throughput). In contrast to some methods that attempt to increase the degree of conversion of toluene or xylene by simply increasing reactor pressures, the superior dispersion and/or dissolution provided by external high shear mixing may allow in many cases a decrease in overall operating pressure while maintaining or even increasing reaction rate. Without wishing to be limited to a particular theory, it is believed that the level or degree of high shear mixing is sufficient to increase rates of mass transfer and may also produce localized non-ideal conditions that enable reactions to occur that might not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006). The high shear mixing device of certain embodiments of the present system and methods is operated under what is believed to be cavitation conditions effective to dissociate the oxygen and toluene or isomeric xylene reactants into free radicals, which then form into the corresponding benzoic acid or methylbenzoic acid isomer, or phthalic acid isomer product.

In some embodiments, the system and methods described herein enable design of a smaller and/or less capital intensive process than previously possible without the use of external high shear mixing device 40. Potential advantages of certain embodiments of the disclosed methods are reduced operating costs and increased production from an existing process. Certain embodiments of the disclosed processes additionally offer the advantage of reduced capital costs for the design of new processes. In embodiments, dispersing oxygen-containing gas in solution prior to catalytic oxidation decreases the amount of unreacted toluene or xylene. Potential benefits of some embodiments of this system and method for the production of benzoic acid or methylbenzoic acid isomers include, but are not limited to, faster cycle times, increased throughput, higher conversion, reduced operating costs and/or reduced capital expense due to the possibility of designing smaller reactors and/or operating the process at lower temperature and/or pressure.

Production of Phthalic Anhydride

Phthalic anhydride (PAN) is the organic compound with the formula $C_6H_4(CO)_2O$, which is an important industrial chemical, for example for the large-scale production of plasticizers. Phthalic anhydride (PAN) may be obtained by catalytic oxidation of ortho-xylene or naphthalene, which is called the Gibbs phthalic anhydride process as shown below:

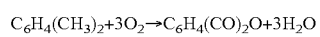

$$C_6H_4(CH_3)_2 + 3O_2 \rightarrow C_6H_4(CO)_2O + 3H_2O$$

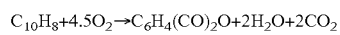

$$C_{10}H_8 + 4.5O_2 \rightarrow C_6H_4(CO)_2O + 2H_2O + 2CO_2$$

In an embodiment, phthalic anhydride (PAN) is produced by reacting an oxidant gas (e.g., oxygen) with liquid ortho-xylene or liquid naphthalene in a HSD at appropriate temperature and pressure in the presence of a suitable catalyst. Suitable catalyst includes vanadium pentoxide or titanium dioxide that may be combined with one or more of the following; antimony oxides caesium. In some cases, sulfur-containing substances and promoters such as Ag, P, Nb, and Sb have been shown to enhance catalyst performance. Alternative catalysts include molybdenum trioxide and calcium oxide, or manganese oxides. In some cases, such catalyst is introduced into the HSD as a slurry. In some cases, such catalyst is introduced into the HSD as part of the liquid feed. In some other cases, such catalyst is constructed as part of HSD. In some cases, the temperature of the HSD is maintained in the range of from about ambient temperature to about 425° C.; alternatively from about 50° C. to about 350° C.; alternatively from about 100° C. to about 320° C. In some cases, the pressure of the HSD is maintained in the range of from about 1 bar to about 60 bar; alternatively from about 1 bar to about 20 bar; alternatively from about 1 bar to about 15 bar.

In an embodiment, phthalic anhydride (PAN) is produced by mixing an oxidant gas with liquid ortho-xylene or liquid naphthalene in a HSD at appropriate temperature and pressure to form a dispersion and then contacting the dispersion with a suitable catalyst to promote the oxidation reaction. In some cases, the temperature of the HSD is maintained in the range of from about ambient temperature to about 425° C.; alternatively from about 50° C. to about 350° C.; alternatively from about 100° C. to about 320° C. In some cases, the pressure of the HSD is maintained in the range of from about 1 bar to about 60 bar alternatively from about 1 bar to about 20 bar; alternatively from about 1 bar to about 15 bar. In some embodiments, contacting the dispersion with a catalyst takes place in a vessel (e.g., a fixed-bed reactor), wherein the vessel is in fluid communication with the HSD. In some embodiments, the vessel is used in conjunction with HSD comprising catalytic surface that promotes the formation of PAN. In some cases, the temperature of the vessel is maintained in the range of from about 50° C. to about 475° C.; alternatively from about 100° C. to about 450° C.; alternatively from about 100° C. to about 300° C. In some cases, the pressure of the vessel is maintained in the range of from about 1 bar to about 150 bar; alternatively from about 1 bar to about 100 bar; alternatively from about 2 bar to about 60 bar. In some embodiments, the oxidation reaction to form PAN also takes place in the HSD during mixing.

Without wishing to be limited by theory, in some cases, the high shear conditions in the HSD induce oxidation reactions needed to produce PAN at bulk temperatures and pressures where the oxidant remains gaseous and ortho-xylene or naphthalene remains liquid. In some embodiments, the dispersion produced in the HSD contains oxidant gas bubbles with a mean diameter of less than 1.5 micron; alternatively less than 1 micron; alternatively less than 0.5 micron; alternatively less than 400 nanometers; alternatively less than 300 nanometers; alternatively less than 200 nanometers.

The product stream exiting the HSD or the vessel contains PAN, unreacted feed (e.g., xylene), and by-products (e.g., maleic anhydride). In some embodiments, the product stream comprising PAN is further processed, such as PAN purification. Purification is well known to those experienced in the art and involves distillation under vacuum and the product is stored either in a molten state or bagged as flakes.

Advantages. Since the oxidation reaction takes place between gaseous oxidant and liquid organic feed (e.g., xylene), there is no need for volatilization of the organic feed and re-condensing, thus reducing energy expenditure. Furthermore, since a catalytic fixed bed may be used instead of a fluidized bed, catalyst removal is no longer necessary as required by conventional processes. Such advantages reduce the complexity and cost of PAN production. The highly exothermic reaction can also be better controlled with the present invention.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A method comprising:
   forming, under high shear, a dispersion comprising gas bubbles of an oxidant consisting essentially of oxygen dispersed in a liquid phase comprising at least one component selected from the group consisting of o-xylene and naphthalene, wherein said gas bubbles have a mean diameter of less than 1.5 micron, and wherein the high shear is provided by a high shear device comprising a catalytic surface comprising an oxidation catalyst;
   contacting said dispersion with the oxidation catalyst to produce a product stream, wherein said product stream comprises phthalic anhydride, wherein the phthalic anhydride in the product stream is substantially pure, and further downstream purification is not utilized.

2. The method of claim 1 wherein the high shear device comprises at least one rotor and at least one complementarily-shaped stator.

3. The method of claim 1 wherein forming the dispersion and contacting the dispersion with the oxidation catalyst take place substantially simultaneously.

4. The method of claim 3 further comprising introducing oxidation catalyst into the high shear device in which the dispersion is formed.

5. The method of claim 1 wherein forming the dispersion under high shear comprises introducing a mixture of the oxidant and the liquid phase into the high shear device.

6. The method of claim 1 wherein the oxidation catalyst contains one or more component(s) selected from the group consisting of antimony, cesium, silver, phosphorus, calcium, and niobium.

7. A method for high shear processing, the method comprising:
   introducing an oxidant consisting essentially of oxygen and a liquid comprising at least one component selected from the group consisting of o-xylene and naphthalene into a high shear device comprising at least one generator comprising a rotor and a complementarily-shaped stator and a catalytic surface comprising an oxidation catalyst, whereby the oxidant and liquid are subjected to high shear conditions to form a dispersion comprising oxidant bubbles dispersed in the liquid; and
   extracting, from the high shear device, a product stream that comprises substantially pure phthalic anhydride.

\* \* \* \* \*